United States Patent
Hurley et al.

(10) Patent No.: US 7,244,760 B2
(45) Date of Patent: Jul. 17, 2007

(54) METHODS FOR PREPARATION AND USE OF PSOROSPERMIN ANALOGS

(75) Inventors: Laurence Hurley, Tucson, AZ (US); Ingrid Fellows, Woodland Hills, CA (US); Michael Kenric Schwaebe, San Diego, CA (US); Jeffrey Paul Whitten, Santee, CA (US)

(73) Assignees: Board of Regents, The University of Texas System, Austin, TX (US); Cylene Pharmaceuticals, Inc., San Diego, CA (US)

( * ) Notice: Subject to any disclaimer, the term of this patent is extended or adjusted under 35 U.S.C. 154(b) by 429 days.

(21) Appl. No.: 10/152,152

(22) Filed: May 20, 2002

(65) Prior Publication Data

US 2003/0120093 A1 Jun. 26, 2003

Related U.S. Application Data

(60) Provisional application No. 60/292,189, filed on May 18, 2001.

(51) Int. Cl.
*C07D 311/80* (2006.01)
*C07D 311/82* (2006.01)
*A61K 31/35* (2006.01)

(52) U.S. Cl. .................. 514/455; 549/391; 549/392

(58) Field of Classification Search ............... 514/455; 540/392, 391
See application file for complete search history.

(56) References Cited

U.S. PATENT DOCUMENTS 6,933,396 B2 * 8/2005 Whitten et al. ............. 549/383

FOREIGN PATENT DOCUMENTS

EP 0 175 376 3/1986 .................. 514/458

OTHER PUBLICATIONS

Lin et al, Chemical Abstracts vol. 125 No. 392826, "Xanthone derivatives as potential anti-cancer drugs", 1996.*
Kwok et al, Proc. Natl. Sci. USA vol. 95 pp. 13531-13536 "Topisomerase II mediated site-directed alkylation . . . " (1998).*
Abou-Shoer et al , Phytochemistry vol. 27 No. 9 pp. 2795-2800 "Antitumor and cytotoxic . . . "(1988).*
Pachuta et al Jol. Nat. Prod. vol. 49 No. 3 pp. 412-423"Antineoplastic agents from higher . . . " (1986).*
Gonda et al., "Studies on the constituents Anaxagorea luzonesis A. Gray," *Chemical & Pharmaceutical Bulletin*, 48:1219-1222, 2000.
Habib et al., "Structure and stereochemistry of psorospermin and related cytotoxic dihydrofuranoxanthones from psorospermun febrifugum," *Journal of Organic Chemistry*, 52:412-418, 1987.
Hano et al., "Constituents of the root bark of morus insignis bur. 1. Structures of four new isoprenylated xanthones morusignins A, B, C and D," *Heteocycles*, 31:1345-1350, 1990.
Hano et al., "Constituents of the root bark of morus insignis bur. 3. Structures of three new isoprenylated xanthones morusignins I, J and K and an isoprenylated flavone morusignin L," *Heterocycles*, 36:1359-1366, 1993.
Jacobs et al., "BMI-1 collaborates with c-Myc in tumorigenesis by inhibiting c-Myc-induced apoptosis via INK4a/ARF," (1999).
Morel et al., "New xanothones from calophyllum caledonicum," *J. Nat. Prod.*, 63:1471-1474. (2000).
Patel et al., "Studies in synthesis of xanothone derivatives. Part VI—Synthesis of furango- & difurano-xanothones," *Indian Journ. Chem.*, 26:1035-1038, 1987.

* cited by examiner

*Primary Examiner*—Thomas McKenzie
*Assistant Examiner*—Raymond Covington
(74) *Attorney, Agent, or Firm*—Fulbright & Jaworski, LLP

(57) ABSTRACT

Psorospermin is a cytotoxic dihydroflranoxanthone that has found to exhibit significant activity against various tumor cell lines. Unfortunately, psorospermin is no longer readily available from its natural plant source. The present invention is directed to a method for preparing psorospermin and psorospermin analogs. Methods are also disclosed for utilizing psorospermin analogs to inhibit cellular proliferation.

6 Claims, 8 Drawing Sheets

Psorospermin Analogues

IC$_{50}$ values ($\mu M$)

| Cell line | Origin | CMPD #30 | CMPD #40 | CMPD #43 | CMPD #48B |
|---|---|---|---|---|---|
| 8226/S | multiple myeloma | 0.036 | 0.485 | 0.095 | 0.200 |
| HL60 | Acute promyelocytic leukemia | 0.012 | 0.230 | 0.037 | 0.076 |
| HL60/AR(adriamycin resistant) | Acute promyelocytic leukemia | 0.011 | 0.240 | 0.045 | 0.110 |
| K562 | Chronic myelogenous leukemia | 0.036 | 0.264 | 0.081 | 0.076 |
| K562/R(daunorubicin resistant) | Chronic myelogenous leukemia | 0.024 | 0.155 | 0.062 | 0.145 |
| A2780 | Ovarian | 0.063 | 0.458 | 0.133 | 0.245 |
| A2780/CP70(cisplatin resistant) | Ovarian | 0.473 | 2.273 | 0.613 | 1.453 |
| MCF7 | Breast, adenocarcinoma | 0.070 | | | |
| MCF 10A | Breast, normal mammary | 0.140 | | | |
| DU 145 | prostate, brain mets | 0.304 | 1.865 | 0.685 | 0.751 |
| LnCAP | prostate, lymph node mets | 0.460 | 2.930 | 0.630 | 1.400 |
| MIA PaCa-2 | pancreas | 0.180 | 1.100 | 0.570 | 0.610 |

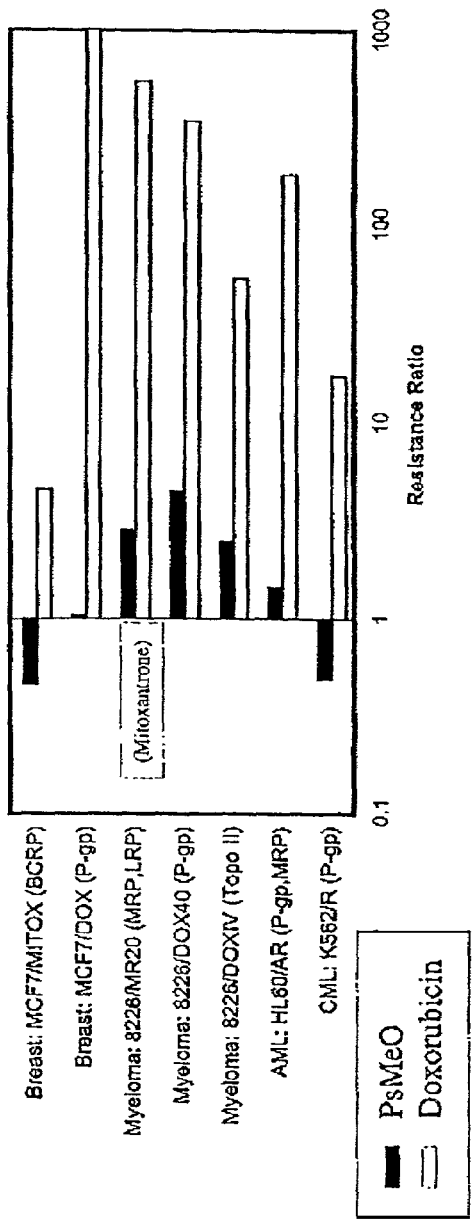
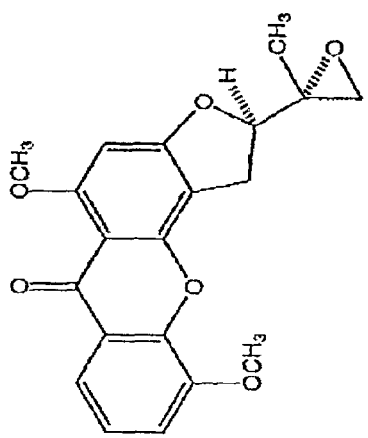
FIG. 7
(±) PsMeO =

Examples of cytotoxicity of psorospermin methyl ether on matched leukemia (A) and lymphoma (B) cell lines, normal (MCF-10A) and neoplastic breast (MCF-7) (C), and pancreatic (MiaPaCa) (D)

METHODS FOR PREPARATION AND USE OF PSOROSPERMIN ANALOGS

The present application claims priority to U.S. Provisional Patent Application Ser. No. 60/292,189, filed May 18, 2001. The entire text of the above-referenced disclosure is specifically incorporated by reference herein without disclaimer. The government owns rights in the present invention pursuant to grant number PF-99-349-01 from the American Cancer Society and grant number CA49751 from the National Institutes of Health.

BACKGROUND OF THE INVENTION

I. Field of the Invention

The present invention relates to fields of chemistry and cell biology generally, and more specifically, to the preparation of psorospermin and psorospermin analogs, and their use as tumor inhibitors.

II. Brief Description of the Prior Art

During the last 20 years, significant advances have been made in elucidating the molecular mechanisms responsible for selective antitumor activity of antitumor agents that target DNA. For example, it is now known that adriamycin is a topoisomerase II poison, that topotecan is a topoisomerase I poison, and that cis-Pt cross-links DNA and may express its selectivity by sequestering or hijacking DNA binding proteins. More recently, signaling pathways leading to apoptosis were uncovered, and the importance of p53 status and the involvement of a multitude of other signaling molecules were inferred. Downstream effectors have become important modulators of antitumor activity, and more specific therapeutic strategies are envisioned using cytostatic agents, differentiation agents, and telomerase inhibitors. These approaches are still experimental, but they hold much hope for a gentler form of cancer treatment.

One promising compound that has been shown to down-regulate downstream effector pathways involving anti-apoptotic factors is psorospermin. Psorospermin is a cytotoxic dihydrofuranoxanthone. Optically active (−) psorospermin is isolated from the roots and stembark of the African plant *psorospermum febrifugum*. Psorospermin is mechanistically related to the pluramycin family of antitumor antibotics, and has been shown to exhibit significant activity in vitro against various tumor cell lines and in vivo against P388 mouse leukemia (Cassady et al., 1990; Kupchan et al., 1980; Kwok et al., 1998).

Psorospermin is particularly intriguing as an anticancer agent because it has low reactivity and poor sequence selectivity toward duplex DNA in comparison to similar compounds such as pluramycins, but at least equal in vitro cytotoxicity and a much more interesting profile in the NCI 60-panel screen (NCI Developmental Therapeutics Web Site). It is believed that a selectivity trigger must exist in vitro, and a variety of suggestions have been made, including DNA-protein cross-links as a consequence of psorospermin-induced abasic sites and topoisomerase I or II as potential cross-linking proteins (Permana et al., 1994).

Unfortunately, optically active (−) psorospermin is no longer readily available from its natural plant source in Africa. Additionally, there are no known methods of synthesizing psorospermin in usable quantities. A need therefore exists for methods of synthesizing psorospermin and psorospermin analogues.

SUMMARY OF THE INVENTION

In accordance with the present invention, there is provided a process of preparing a furanoxanthone compound from which psorospermin analogs may be produced, the furanoxanthone having a formula:

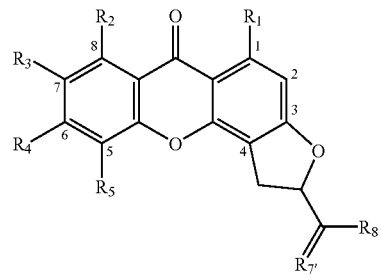

wherein $R_1$ is H, OH, O-alkyl, $OCH_3$, halogen, or alkyl; $R_2$-$R_4$, is H, OH, O-alkyl, $OCH_3$, halogen, or alkyl; $R_5$ is H, O-alkyl, or alkyl; $R_7$, is CHR, where R is alkyl or H; and $R_8$ is H or alkyl.

The process comprises obtaining a first compound having a formula:

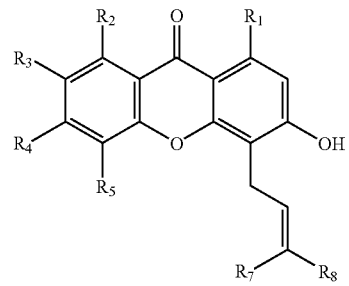

wherein $R_1$ is H, OH, O-alkyl, $OCH_3$, halogen, or alkyl; $R_2$-$R_4$, is H, OH, O-alkyl, $OCH_3$, halogen, or alkyl; $R_5$ is H, O-alkyl, or alkyl; $R_7$ is $CH_2R$, where R is alkyl or H; and $R_8$ is H or alkyl, and reacting this first compound with $Pd((CH_3CN)_4(BF_4)_2)$ or $Pd(OCOCF_3)_2$ and benzoquinone in DMSO. In one preferred embodiment the reaction takes place between 15° C. and 30° C. In one embodiment, the first compound has the following formula:

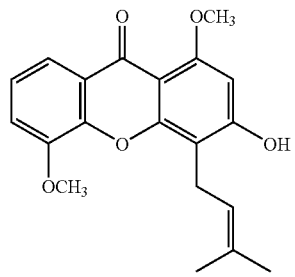

and the resulting furanoxanthone compound has the following formula.

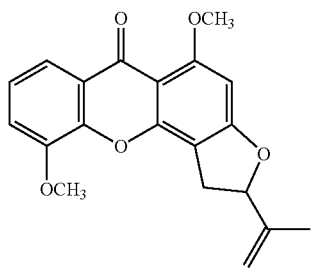

There is also provided a process for preparing psorospermin analogs having a formula:

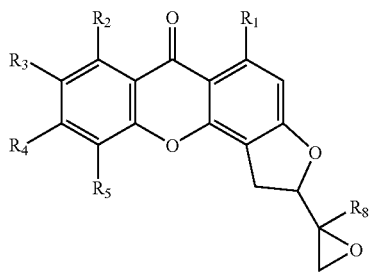

wherein $R_1$ is H, OH, O-alkyl, OCH$_3$, halogen, or alkyl; $R_2$-$R_4$, is H, OH, O-alkyl, OCH$_3$, halogen, or alkyl; $R_5$ is H, O-alkyl, or alkyl; and $R_8$ is H or alkyl. The process comprises obtaining a first compound having a formula:

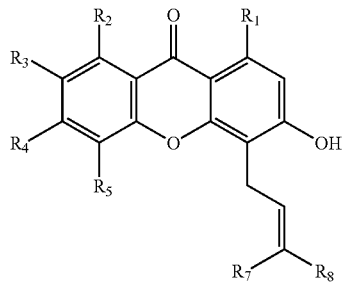

wherein $R_1$ is H, OH, O-alkyl, OCH$_3$, halogen, or alkyl; $R_2$-$R_4$, is H, OH, O-alkyl, OCH$_3$, halogen, or alkyl; $R_5$ is H, O-alkyl, or alkyl; $R_7$ is CH$_2$R, where R is alkyl or H; and $R_8$ is H or alkyl, and reacting this first compound with Pd((CH$_3$CN)$_4$(BF$_4$)$_2$) and benzoquinone in DMSO or with Pd(OCOCF$_3$)$_2$ and benzoquinone in DMSO. The reaction may further comprise performing an epoxidation or an epoxide forming reaction. In one embodiment, the psorospermin analogs may have an absolute configuration of (±)(2'R*, 3'R*) or (±)(2'R*,3'S*).

In another ebodiment, there is provided a process for preparing (–) psorospermin analogs having a formula:

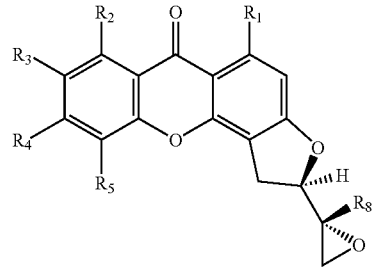

wherein $R_1$ is H, OH, O-alkyl, OCH$_3$, halogen, or alkyl; $R_2$-$R_4$, is H, OH, O-alkyl, OCH$_3$, halogen, or alkyl; $R_5$ is H, O-alkyl, or alkyl; and $R_8$ is H or alkyl. The process comprises obtaining a first compound having a formula:

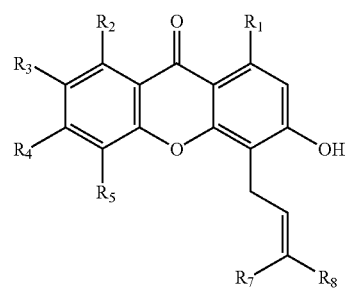

wherein $R_1$ is H, OH, O-alkyl, OCH$_3$, halogen, or alkyl; $R_2$-$R_4$, is H, OH, O-alkyl, OCH$_3$, halogen, or alkyl; $R_5$ is H, O-alkyl, or alkyl; an $R_7$ is CH$_2$R, where R is alkyl or H; and $R_8$ is H or alkyl, and reacting this first compound with Pd((CH$_3$CN)$_4$(BF$_4$)$_2$) and benzoquinone in DMSO or with Pd(OCOCF$_3$)$_2$ and benzoquinone in DMSO to yield a second compound. The process further comprises performing an asymmetric dihydroxylation of the second compound. The process third compound comprising (+) disastereomers and (–) diastereomers, isolating the (–) diastereomers of the third compound, and performing and epoxidation or an epoxide forming reaction.

In one embodiment, the resulting psorospermin analogs may have an absolute configuration of (–)(2'R, 3'R) or (–)(2'R, 3'S). Additionally, the asymmetric dihydroxylation may comprise reacting the first compound with (1) tBu-OH, CH$_3$CN, H$_2$O, OsO$_4$, and a chiral ligand, (2) a chiral ligand, K$_3$Fe(CN)$_6$, K$_2$CO$_3$, and K$_2$OsO$_4$·2 H$_2$0, or (3) tBu-OH, CHCl$_3$, H$_2$O, OsO$_4$, and a chiral ligand. The (–) diastereomers of the third compound may be isolated by chromatography.

In yet another embodiment, a process is provided for preparing a (–) psorospermin analog having a formula:

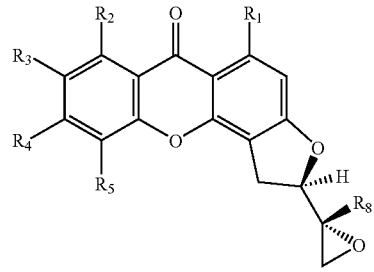

wherein $R_1$ is H, OH, O-alkyl, OCH$_3$, halogen, or alkyl; $R_2$-$R_4$, is H, OH, O-alkyl, OCH$_3$, halogen, or alkyl; $R_5$ is H, O-alkyl, or alkyl; and $R_8$ is H or alkyl. The process comprises obtaining a first compound having a formula:

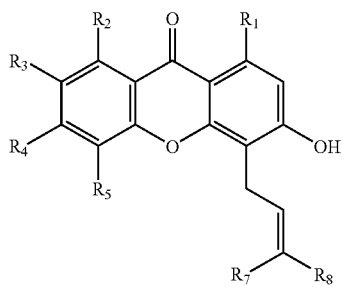

wherein $R_1$ is H, OH, O-alkyl, $OCH_3$, halogen, or alkyl; $R_2$-$R_4$, is H, OH, O-alkyl, $OCH_3$, halogen, or alkyl; $R_5$ is H, O-alkyl, or alkyl; $R_7$ is $CH_2R$, where R is alkyl or H; and $R_8$ is H or alkyl, and reacting the first compound with chiral ligand, $Pd((CH_3CN)_4(BF_4)_2)$, and benzoquinone in DMSO or with a chiral ligand, $Pd(OCOCF_3)_2$, and benzoquinone in DMSO. In one preferred embodiment, the chiral ligand may comprise ip-boxax, bisoxaxoline binapthyl, or spiro-bis (isoxazoline). The process may also comprise performing an epoxidation or an epoxide forming reaction. The resulting psorospermin analogs may have an absolute configuration of (−)(2'R, 3'R) or (−)(2'R, 3'S).

In another embodiment, a process is disclosed for preparing a psorospermin analog having a formula:

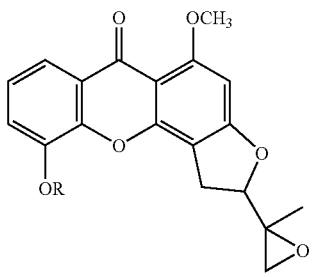

wherein R is hydrogen, an alkyl, a hydroxyl, a hydroxyalkyl, a halogen, a benzyl, an amine, an alkylamine, a thiol, or an alkylthiol. The process comprises obtaining a first compound having a formula:

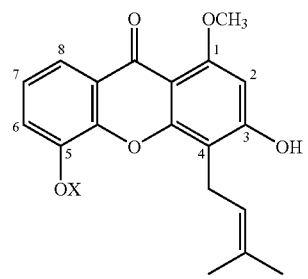

wherein X is a protecting group, reacting the first compound with $Pd((CH_3CN)_4(BF_4)_2)$ benzoquinone in DMSO or with $Pd(OCOCF_3)_2$ and benzoquinone in DMSO, performing a deprotection reaction, introducing the R group at the oxygen located at the 5' position, and performing an epoxidation or epoxide forming reaction.

The step of introducing the R group may comprise performing a chemical reaction with an alkylating agent and a base. In one preferred embodiment, introducing the R group comprises performing a chemical reaction with $CH_3I$ and $K_2CO_3$, AcCl and $K_2CO_3$, or BnBr and $K_2CO_3$. The protecting group, X, may comprise tert-butyl silane.

In yet another embodiment, a method is provided for preparing a psorospermin analog having a formula:

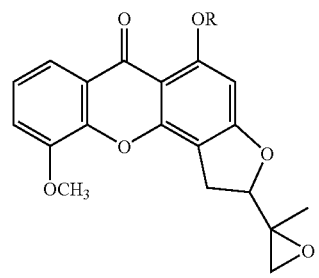

wherein R is a hydrogen, an alkyl, a hydroxyl, a hydroxyalkyl, a halogen, a benzyl, an amine, an alkylamine, a thiol, or an alkylthiol. The method comprises obtaining a first compound having a formula:

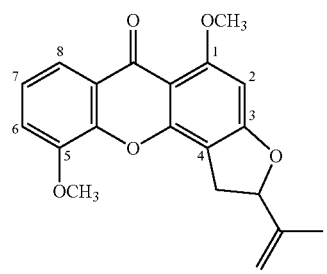

performing a reaction to remove the $CH_3$ group from the oxygen at the 1 position, performing a chemical reaction with an alkylating agent and a base, and performing an epoxidation or an epoxide forming reaction. In one embodiment, the performing a reaction to remove the $CH_3$ group from the oxygen at the 1 position may comprise performing a chemical reaction using $BCl_3$. The performing a chemical reaction with an alkylating agent and a base may comprise performing a chemical reaction with EtI and $Cs_2CO_3$, isopropyl bromide, KI, $Cs_2CO_3$, AcCl and $K_2CO_3$, or BnBr and $K_2CO_3$.

A method of inhibiting cell proliferation is also provided. The method comprises contacting a cell with an effective amount of a compound having the following formula:

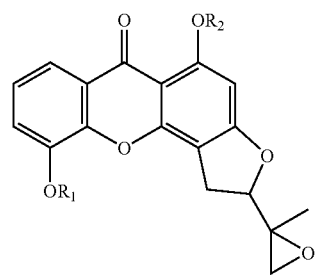

wherein $R_1$ and $R_2$ are independently hydrogen, a benzyl, an alkyl, an acetyl, a hydroxyl, a hydroxyalkyl, a halogen, an amine, an alkylamine, a thiol, or an alkylthiol. The cell may be a cancer cell, and more particularly may be a pancreatic cancer cell, a prostate cancer cell, a leukemias cell, a lymphomas cell, a myeloma cell, an ovarian cancer cell, or a breast cancer cell. The cancer cell may also be a multi-drug resistant (MDR) cancer cell. The MDR cancer cell may be resistant to a topoisomerase II inhibitor and may be mediated by MRP-1 or glycoprotein. The cell may also be in a mammal.

A method is also provided for directing the sequence-specific alkylation of DNA. The method comprises contacting a cell with an effective amount of a compound having the following formula:

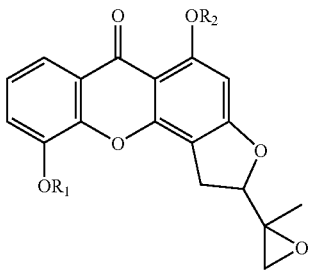

wherein $R_1$ and $R_2$ are independently hydrogen, a benzyl, an alkyl, an acetyl, a hydroxyl, a hydroxyalkyl, a halogen, an amine, an alkylamine, a thiol, or an alkylthiol. In another embodiment, a method is provided for inhibiting the activity of topoisomerase II, the method comprising contacting a cell with an effective amount of a compound having the following formula:

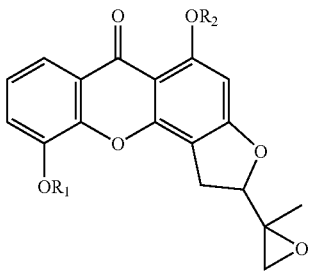

wherein $R_1$ and $R_2$ are independently hydrogen, a benzyl, an alkyl, an acetyl, a hydroxyl, a hydroxyalkyl, a halogen, an amine, an alkylamine, a thiol, or an alkylthiol.

In yet another embodiment, a method of down-regulating oncogenes is provided. The method comprises contacting a cell with an effective amount of a compound having the following formula:

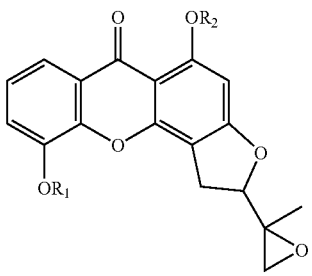

wherein $R_1$ and $R_2$ are independently hydrogen, a benzyl, an alkyl, an acetyl, a hydroxyl, a hydroxyalkyl, a halogen, an amine, an alkylamine, a thiol, or an alkylthiol. The oncogene may be BMI-1.

In a further embodiment, a method is provided for identifying patients with a BMI-1 related cancer. The method comprises obtaining a first sample from a patient, measuring the amount of BMI-1 protein or nucleic acid in the first sample, comparing the amount of BMI-1 protein or nucleic acid in the first sample with a second sample obtained from a non-cancerous subject, wherein an increased amount of BMI-1 protein or nucleic acid in the first sample relative to the second sample indicates a BMI-1 related cancer.

Additionally, the present invention is also directed to pharmaceutical compositions comprising a compound having the formula:

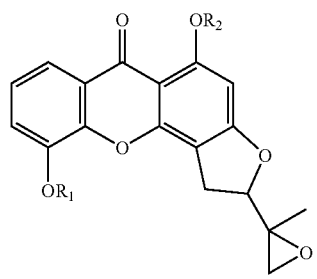

wherein $R_1$ and $R_2$ are independently hydrogen, a benzyl, an alkyl, an acetyl, a hydroxyl, a hydroxyalkyl, a halogen, an amine, an alkylamine, a thiol, or an alkylthiol.

A psorospermin analog is also disclosed, the psorospermin analog having a formula:

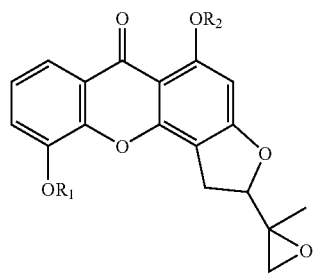

wherein $R_1$ and $R_2$ are independently hydrogen, a benzyl, an alkyl, an acetyl, a hydroxyl, a hydroxyalkyl, a halogen, an amine, an alkylamine, a thiol, or an alkylthiol.

Additionally, the present invention is also directed to a compound having the formula:

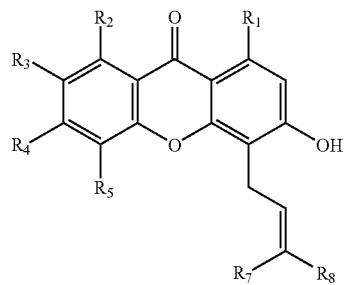

wherein $R_1$-$R_5$, and $R_7$-$R_8$ are independently hydrogen, a phenyl, an alkyl, a hydroxyl, a hydroxyalkyl, a halogen, an amine, an alkylamine, a thiol, or an alkylthiol.

The present invention also comprises a process of preparing a compound of the formula:

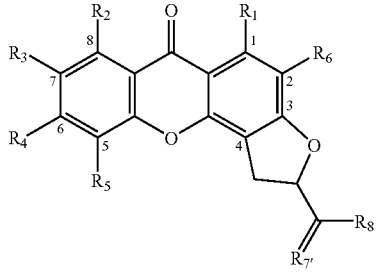
(1)

wherein each $R_1$-$R_4$ and $R_6$ is independently H, OH, O-alkyl, halogen, or alkyl;
$R_5$ is H, O-alkyl, or alkyl;
$R_{7'}$ is $CH_2$; and
$R_8$ is H or alkyl;
the process comprising:
reacting compound of the formula:

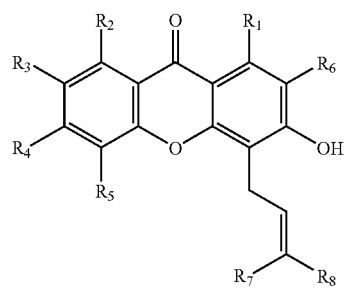

wherein $R_1$-$R_6$ and $R_8$ are as defined above, and $R_7$ is $CH_3$;
with $Pd((CH_3CN)_4(BF_4)_2)$ or $Pd(OCOCF_3)_2$ and benzoquinone in DMSO.

The process may comprise reaction at a temperature between 15° C. and 30° C. The compound of formula (2) may have the formula:

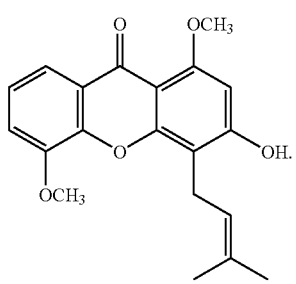

In another embodiment, there is provided a process for preparing psorospermin analogs of the formula.

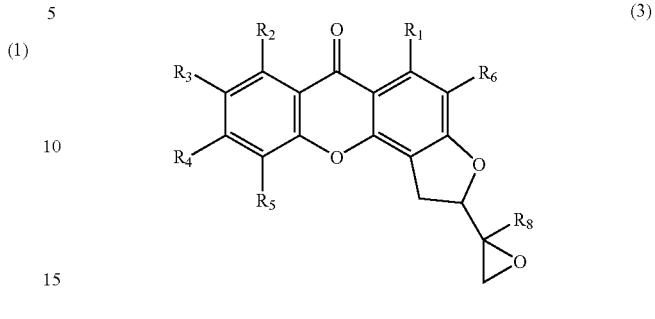
(3)

each of $R_1$-$R_4$ and $R_6$ is independently H, OH, O-alkyl, halogen, or alkyl;
$R_5$ is H, O-alkyl, or alkyl; and
$R_8$ is H or alkyl;
the process comprising effecting dihydroxylation followed by epoxidation of a compound of the formula:

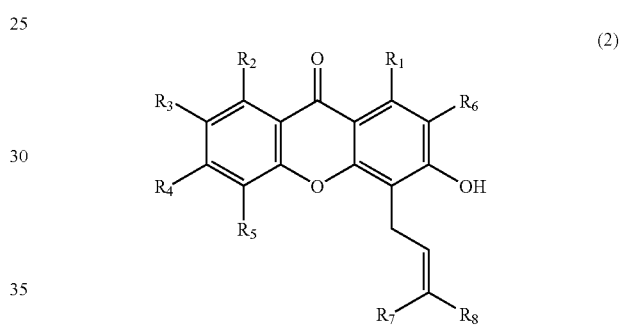
(2)

wherein $R_1$-$R_5$ and $R_8$ are as defined in claim 1, and $R_7$ is $CH_3$.

The process may further comprising performing chiral separation. The compounds of formula (3) may have an absolute configuration of (±)(2'R*, 3'R*) or (±)(2'R*,3'S*).

In still another embodiment, there is provided a process for preparing (−)analogs having a formula:

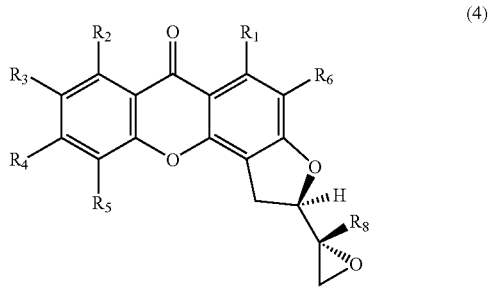
(4)

wherein each of $R_1$-$R_4$ and $R_6$ is independently H, OH, O-alkyl, $OCH_3$, halogen, or alkyl;
$R_5$ is H, O-alkyl, or alkyl; and
$R_8$ is H or alkyl;
the process comprising performing chiral separation chromatography on an unresolved mixture of stereoisomers of a compound of the formula:

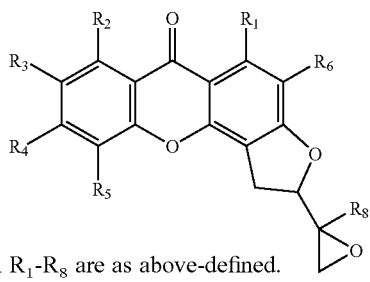

wherein $R_1$-$R_8$ are as above-defined.

In still a further embodiment, there is provided a process for preparing a psorospermin analog having a formula:

(5)

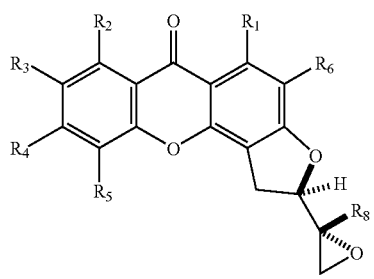

wherein each of $R_1$-$R_4$ and $R_6$ is independently H, OH, O-alkyl, halogen, or alkyl;

$R_5$ is H, O-alkyl, or alkyl; and $R_8$ is H or alkyl;

the process comprising:

treating a compound of the formula:

(1)

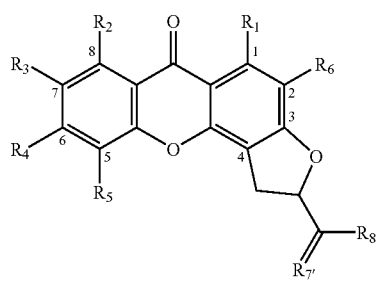

wherein $R_1$-$R_6$ and $R_8$ are defined above and $R_{7'}$ is $CH_2$;

with a dihydroxylating agent and a chiral ligand to obtain a dihydroxylated product, followed by epoxidation of the dihydroxylated product.

There also is provided method of inhibiting cell proliferation, the method comprising contacting a cell with an effective amount of a compound having the formula:

(3)

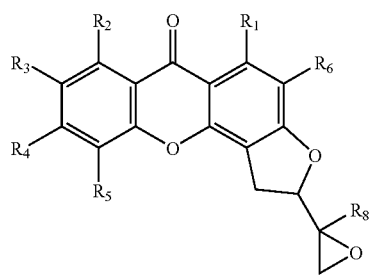

wherein $R_1$-$R_8$ are as defined in claim 1.

The cell may be a cancer cell.

Another method is provided, this to inhibit proliferation of a cancer cell, wherein the cancer cell is a pancreatic cancer cell, prostate cancer cell, myeloma cell, ovarian cancer cell, or breast cancer cell, which comprises contacting said cell with an effective amount of a compound of the formula:

(3)

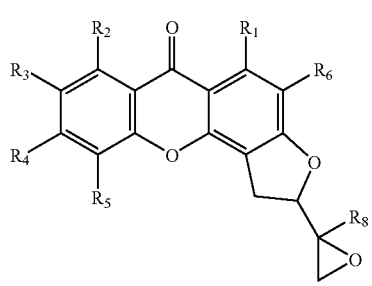

wherein $R_1$-$R_4$, $R_6$ and $R_8$ are as defined in claim 1 and $R_5$ is H, OH, O-alkyl or alkyl. The cancer cell may be a multi-drug resistant (MDR) cancer cell, and the MDR cancer cell may be resistant to a topoisomerase II inhibitor. The MDR may be mediated by MRP-1 or glycoprotein. The cell may be in a mammal.

In still a further embodiment, there is provided a method of directing the sequence-specific alkylation of DNA, comprising contacting a cell with an effective amount of a compound of the formula:

(3)

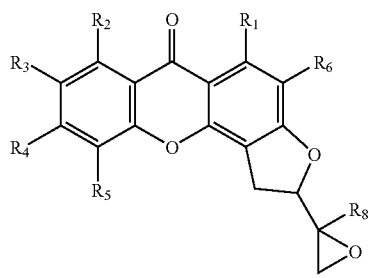

wherein $R_1$-$R_4$, $R_6$ and $R_8$ are as defined in claim 1 and $R_5$ is H, OH, O-alkyl or alkyl.

Also provided is a method of inhibiting the activity of topoisomerase II, comprising contacting a cell with an effective amount of a compound of the formula:

(3)

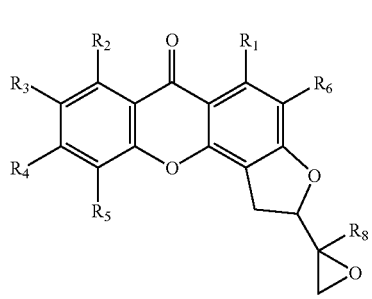

wherein $R_1$-$R_4$, $R_6$ and $R_8$ are as defined in claim 1 and $R_5$ is H, OH, O-alkyl or alkyl.

Another provided method, for down-regulating oncogenes, comprises contacting a cell with an effective amount of a compound of the formula:

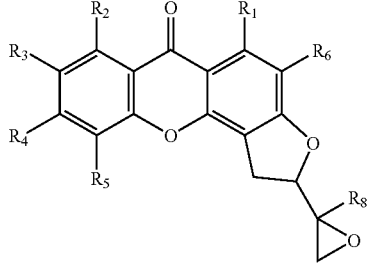

(3)

wherein $R_1$-$R_4$, $R_6$ and $R_8$ are as defined in claim 1 and $R_5$ is H, OH, O-alkyl or alkyl.

The oncogene may be BMI-1.

Yet another embodiment provides for a method for identifying patients with a BMI-1 related cancer, the method comprising (a) obtaining a first sample from a patient; (b) measuring the amount of BMI-1 protein or nucleic acid in the first sample; (c) comparing the amount of BMI-1 protein or nucleic acid in the first sample with a second sample obtained from a non-cancerous subject; wherein an increased amount of BMI-1 protein or nucleic acid in the first sample relative to the second sample indicates a BMI-1 related cancer.

Also provided is a pharmaceutical composition comprising a compound of the formula:

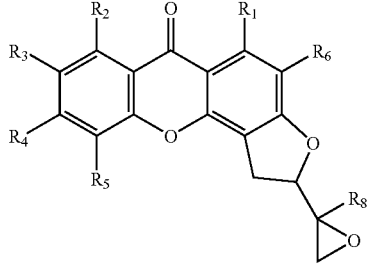

(3)

each of $R_1$-$R_4$ and $R_6$ is independently H, OH, O-alkyl, halogen, or alkyl;
$R_5$ is H, O-alkyl, or alkyl; and
$R_8$ is H or alkyl.

Another provided method for treating a subject with a hyperproliferative disorder comprises administering to the subject a compound of the formula:

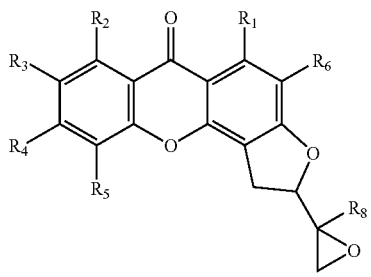

(3)

each of $R_1$-$R_4$ and $R_6$ is independently H, OH, O-alkyl, halogen, or alkyl;

$R_5$ is H, O-alkyl, or alkyl; and
$R_8$ is H or alkyl.

The method may further comprise treating the subject with one or more of chemotherapy, radiotherapy, immunotherapy, gene therapy, or surgery.

Another provided compound has the formula:

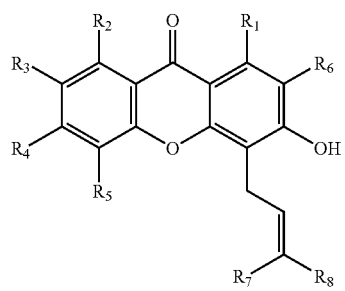

(2)

wherein each of $R_1$-$R_4$ and $R_6$ is H, OH, O-alkyl, halogen, or alkyl;
$R_5$ is H, O-alkyl, or alkyl;
$R_7$ is $CH_3$; and
$R_8$ is H or alkyl;
or:

(1)

wherein each of $R_1$-$R_4$ and $R_6$ is independently H, OH, O-alkyl, halogen, or alkyl;
$R_5$ is H, O-alkyl, or alkyl;
$R_{7'}$ is $CH_2$; and
$R_8$ is H or alkyl;
or:

(3)

wherein each of $R_1$-$R_4$ and $R_6$ is independently H, OH, O-alkyl, halogen, or alkyl;
$R_5$ is H, O-alkyl, or alkyl; and
$R_8$ is H or alkyl;
or:

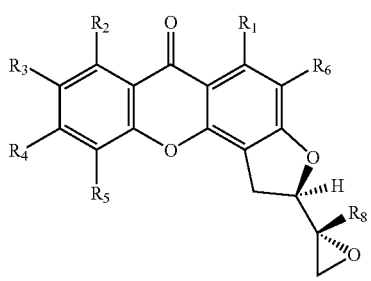

(5)

wherein each of $R_1$-$R_4$ and $R_6$ is independently H, OH, O-alkyl, halogen, or alkyl;
$R_5$ is H, O-alkyl, or alkyl; and
$R_8$ is H or alkyl.

These compounds may have $R_6$ being H. These compounds may have $R_2$-$R_4$ and $R_6$ being H. These compounds may have $R_8$ being methyl. These compounds may have $R_5$ being $OCH_3$ and $R_1$ being O-alkyl or OH.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6 shows $IC_{50}$ values for various psorospermin analogs.

FIG. 7 shows a comparison of sensitivity of matched cell lines to doxorubicin and psorospermin methyl ether.

DETAILED DESCRIPTION OF THE INVENTION

I. The Present Invention

Figure 1:
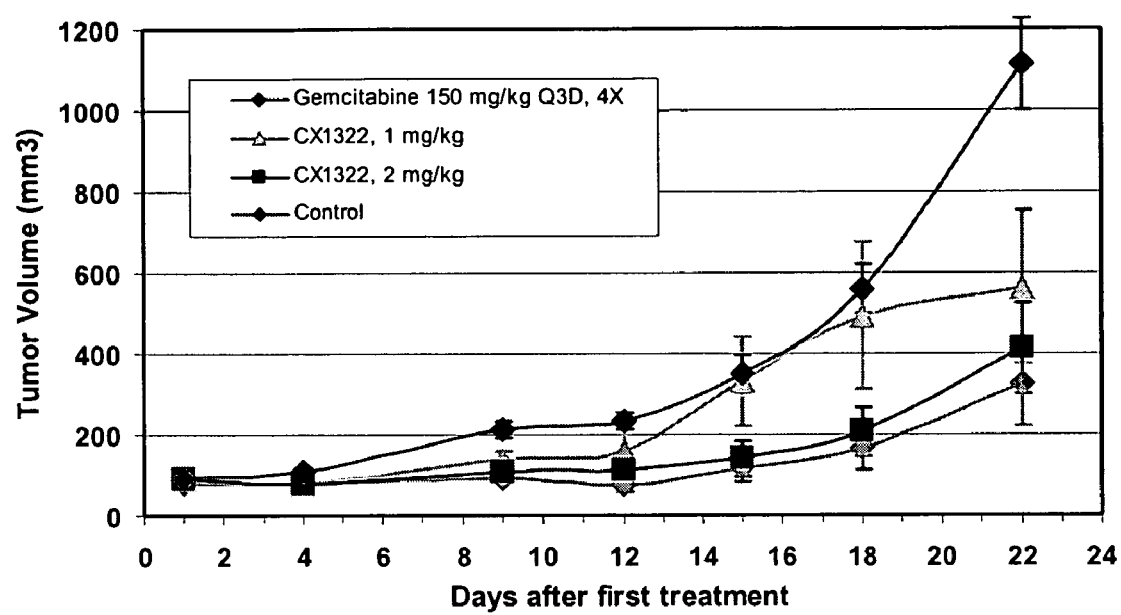
FIG. 1 shows the structure of psorospermin.

Psorospermin, shown in FIG. 1, is a potent DNA alkylating antitumor agent. While the exact molecular mechanisms responsible for the biological activities of psorospermin are unknown, it is believed that the antitumor activity of psorospermin is related to its interaction with the DNA-topoisomerase II complex. This blocks other cellular enzyme functions, and eventually leads to cell death.

Some of the psorospermin analogs disclosed herein may also be used to down-regulate downstream effector pathways involving anti-apoptotic factors such as BMI-1. Psorospermin analogs are predicted to have significant advantages over the presently available clinically effective topoisomerase II poisons, such as doxorubicin and mitoxanthone, or alkylators, such as cyclophosphamide and BCNU, even though these compounds are among the most successful antitumor agents.

Currently, there are no known methods for synthesizing psorospermin analogs in usable quantities. The term "psorospermin analogs" as used herein is intended to include both psorospermin itself and analogs thereof. Furthermore, psorospermin is no longer available from its natural plant source in Africa. The present invention provides a synthetic method for producing quantities of psorospermin analogs from commercially available starting materials. This is made possible by the use of a new cyclization reaction to form a key benzofuran moiety that can be reacted further to yield the psorospermin analogs. Furthermore, the reaction can be modified to produce optically active (−) psorospermin analogs. This is desirable as the optically active (−) compounds are thought to be particularly effective antitumor agents.

II. Topoisomerase II

Type II topoisomerases are essential nuclear enzymes that regulate the topological status of DNA (Wang, 1996). The topoisomerase II catalytic cycle consists of several discrete steps. First, topoisomerase II forms a noncovalent complex with duplex DNA. In the presence of $Mg^{2+}$, a double-stranded DNA cleavage and re-ligation equilibrium is then established at the prestrand passage stage, with a topoisomerase II tyrosine residue attached to the 5'-phosphate of the broken DNA. Next, after the binding of ATP, an intact DNA duplex is passed through the transient double-stranded break site (or "gate site"). A poststrand passage equilibrium involving DNA breakage and re-ligation is then established. Finally, after the re-ligation, ATP is hydrolyzed to facilitate enzyme turnover and the initiation of a subsequent cycle (Watt et al., 1994; Osheroff et al., 1991; Robinson et al., 1991).

III. Psorospermin as a Topoisomerase II Inhibiting Agent

It has been demonstrated that interaction of psorospermin with the topoisomerase II-DNA complex produces a topoisomerase II site-directed alkylation of DNA that takes place at a step prior to formation of the topoisomerase II-DNA covalent complex (Hansen et al., 1996; Kwok et al., 1998; Kwok and Hurley, 1998). In addition to alkylation, other causes of antitumor activity may be: (1) topoisomerase II poison—the alkylation may trap the covalently bound DNA/topoisomerase II complex, interfering with the breaking/rejoining reaction, (2) reversible topoisomerase II cleavage, resulting in depurinated, abasic sites, and (3) catalytic inhibitor of topoisomerase cleavage.

A. Structure of the Psorospermin-(N7-guanine)-DNA Adduct

Figure 2:
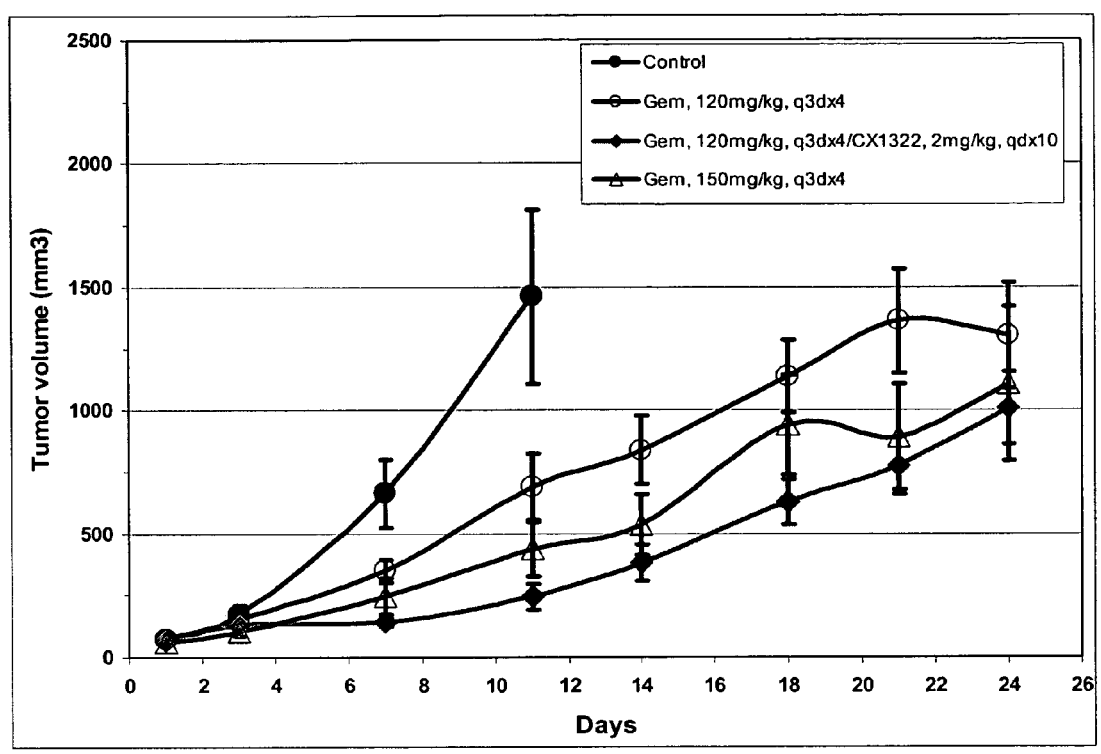
FIG. 2 shows the reaction of psorospermin with N7 guanine in DNA.

Gel electrophoresis and high-field NMR have previously been used to define a mechanism for covalent reaction with N7 of guanine in DNA, shown in FIG. 2, and to determine the DNA sequence selectivity for this covalent reaction (Hansen et al., 1996). Psorospermin is between $10^1$ and $10^2$ less reactive than the pluramycins. Also, unlike the pluramycins, there is no selectivity for the base pair to the 3' side of the alkylated guanine, but there is a distinct selectivity for the base pair to the 5' side.

Figure 3:
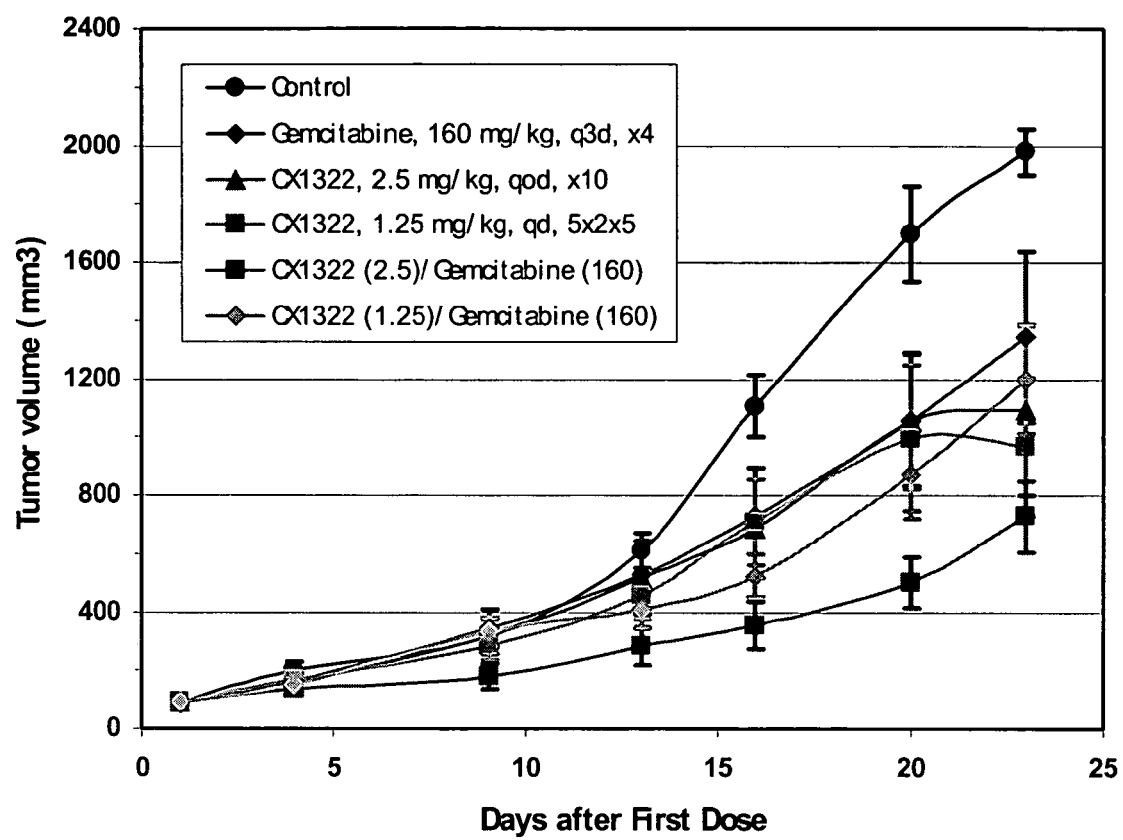
FIG. 3 shows a diagrammatic summary of NOESY connectivities between psorospermin and the major groove; the intermolecular connectivities show that the long axis of the intercalating chromophore lies in a roughly parallel orientation to the adjoining base pairs.

For both high- and medium-reactivity sites, psorospermin shows the greatest preference for a guanine located to the 5' side, a second preference for an adenine in the 5' position, and only low reactivity with guanines having a pyrimidine at the same position. Like the pluramycins, psorospermin intercalates into the DNA and positions the reactive epoxide into the proximity of the guanine that is located to the 3' side of the intercalation site. NMR results indicate that covalent attachment occurs between N7 of guanine and C4' of the epoxide on the psorospermin ligand. See FIG. 3. However, despite these similarities, the proposed precovalent mode of DNA binding is more similar to the acridine class of agents than to the pluramycins (Hansen et al., 1996). Like the acridines, psorospermin stacks its aromatic chromophore in an orientation parallel to the adjoining base pairs, as opposed to an orthogonal orientation characteristic of the pluramycins (Hansen and Hurley, 1995; Sun et al., 1995; Hansen, Yun, and Hurley, 1995).

In this respect, the psorospermin-DNA interaction resembles that of the quinacrine nitrogen mustard (Baguley, 1991; Gopalakrishnan et al., 1992). This parallel, as opposed to orthogonal, orientation to the base pairs is important because it illustrates that maximizing base-stacking interactions is critical for stabilization of the complex prior to covalent alkylation in the absence of significant groove interactions. Furthermore, even with these enhanced base-pair stacking interactions, psorospermin has only a modest to poor alkylation ability. This is important because the alkylation sequence selectivity is determined by a site-directed alkylation by topoisomerase II, and in order to achieve maximum selectivity, it is preferable that the covalent reactivity in the absence of topoisomerase II is minimal.

B. Topoisomerase II Directs Site-Directed Alkylation of DNA by Psorospermin

Topoisomerase II directs the sequence-specific alkylation of DNA by psorospermin. In comparison, pluramycin alkylation is inhibited with increasing topoisomerase II concentration. While psorospermin shows poor sequence selectivity and reactivity with DNA in a cell-free system, in in vitro systems it shows a much higher reactivity and a sequence selectivity that is directed by topoisomerase II. The stereochemical requirement dictates why topoisomerase II enhancement of psorospermin occurs, while pluramycin is unaffected.

Figure 4:
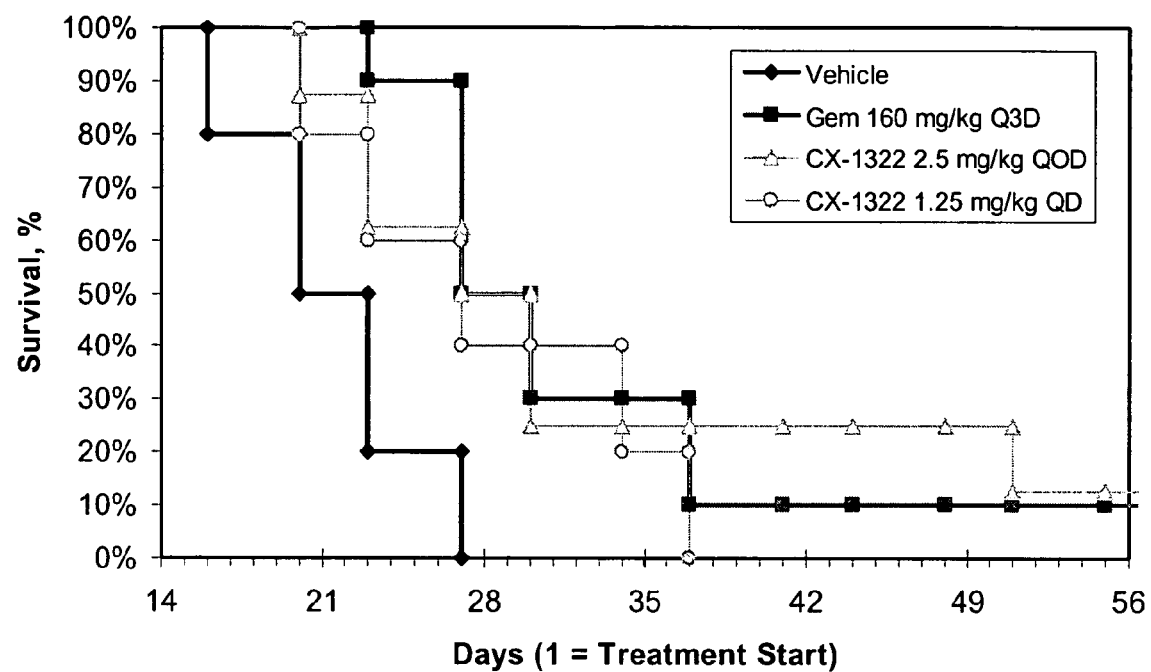
FIG. 4 shows the topoisomerase II cleavage products indicated as site A and site B.

In the absence of psorospermin, the intensity of the topoisomerase II-mediated DNA cleavage is much less at site B than at site A. As the concentration of psorospermin was increased, the topoisomerase II-mediated DNA cleavage at site A was decreased, while the cleavage at site B was enhanced. The psorospermin-induced DNA cleavage by topoisomerase II reaches a maximum of 3-fold at a 10 μM drug concentration (FIG. 4). This result suggests that psorospermin alkylation at site B traps the topoisomerase II-DNA complex at this site. On the other hand, the cleaved complex formation at site A was reduced in the presence of psorospermin, despite the 3-fold enhancement of psorospermin alkylation at site A.

Figure 5:
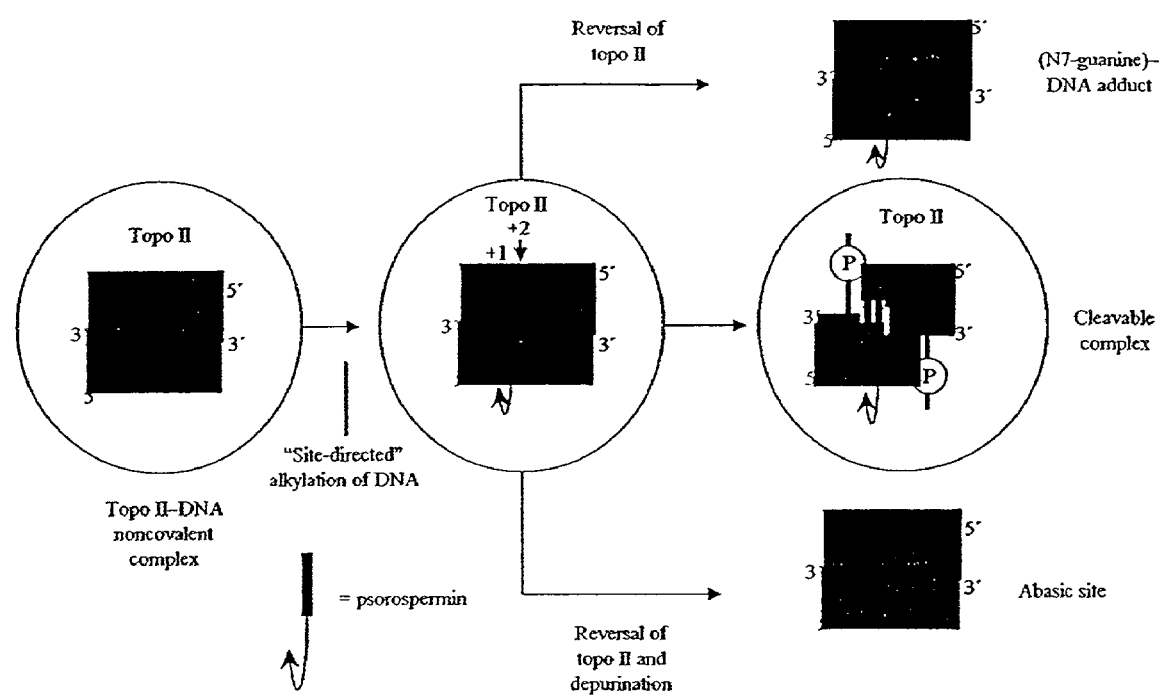
FIG. 5 shows the possible biochemical consequences of site-directed alkylation of DNA by psorospermin.

Sites A and B are three base pairs apart from each other, and *Drosophila* topoisomerase II binds a region of approximately 23 base pairs, based on the results of a DNase I footprinting experiment (Lee et al, 1989). Therefore, it is likely that sites A and B are competing with each other for topoisomerase II binding, and the 25-fold enhancement of the psorospermin alkylation at site B dominates this competition. FIG. 5 summarizes the three possible biochemical consequences of the site-directed alkylation of DNA by psorospermin. Because psorospermin is a 7-alkyl adduct, depurination occurs slowly at room temperature over a period of several days.

A number of clinically important anticancer drugs have been shown to kill tumor cells by targeting topoisomerase II (Osheroff et al., 1997; Liu, 1989). There are a number of modes of DNA binding of topoisomerase II poisons, as shown in Table 1 (Capranico and Binaschi, 1998).

TABLE 1

Mode of DNA binding of eukaryotic DNA topoisomerase poisons.

| DNA binding mode | Pure intercalators | Groove binders | Mixed groove binders/ intercalators |
|---|---|---|---|
| Topoisomerase IB-specific | | Bulgarein Terbenzimidazoles | Indolocarbazoles |
| Topoisomerase II-specific | Ellipticines Flavones | Streptonigrin | Anthracyclines mAMSA Bisantrene Mitoxantrone, piroxantrone Amonafide Quinolones |
| Dual poisons | Saintopin Intoplicine Protoberberines Fagaronine | — | Actinomycins D NSC 665517 |

Of the three types—pure intercalators, groove binders, and mixed groove binders/intercalators—the mixed binding mode compounds are the most effective as topoisomerase II poisons. Belonging to this group are the clinically effective anthracyclines, mAMSA, and quinolones. Psorospermin does not fit under any of these established groups. Instead, it belongs to a fourth group that may be termed the covalent intercalator type. Psorospermin is set apart from these other agents from a mechanistic/structural basis.

The site selectivity (e.g., sequence selectivity around intercalation or groove binding sites) differs from one group of topoisomerase II poisons to another (e.g., A−1, A+1 for doxorubicin and C/T−1, G+1 for mitoxanthone), and generally within one class there is a correlation between cytotoxicity and production of double-strand breaks (Pommier et al., 1989; Covey et al., 1988; Zwelling et al., 1981). However, between different drug classes that cleave at different sites, there is no correlation between cytotoxicity and double-strand breaks, suggesting that cleavage at different sites in the genome may lead to different biological consequences (Pommier et al., 1989; Covey et al., 1988; Zwelling et al., 1981).

For etoposide and mAMSA, the sites of topoisomerase II-induced cleavage in vivo are different (Pommier et al, 1992). In the c-myc protooncogene, only nAMSA cleaves at the $P_2$ promoter (Pommier et al., 1992). In one case the effect of different analogs of doxorubicin on site selectivity of topoisomerase II was determined and found to be different (Capranico et al., 1995). It may be inferred that drug-directed topoisomerase II cleavage is dependent not only on the class of drug (e.g., anthracycline vs. quinolone), but also upon the unique steric and electronic characteristics of the drug molecule. Therefore, different analogs of psorospermin should be site-directed to alkylate different guanine sites by topoisomerase II α and β.

A summary of the advantages of psorospermin over existing topoisomerase II poisons is shown in Table 2.

TABLE 2

| Cytotoxic Drug Failure Mechanism | Psorospermin or Analogs | Anticipated Result |
| --- | --- | --- |
| Reversible ternary complex (topoisomerase II-DNA-drug) | Covalent N7-alkyl G-adduct | Enhanced dwell time on topoisomerase II |
| Mutant topoisomerase II | Intercalation at +1 to +2 rather than −1 to +1 gate site for other drugs | Significantly reduced cross-resistance in topoisomerase II cell lines |
| Nonspecific DNA alkylation | Topoisomerase II-mediated site-directed alkylation | Greatly enhanced DNA sequence specificity |
| Downstream oncogene (e.g., BCL-2 or BMI-1) mediated drug resistance | Site-directed alkylation in oncogene | Restoration of pro-apoptosis signaling |

C. The Topoisomerase II Induced DNA Cleavage by Psorospermin is Reversible

The alkylating site within the topoisomerase II gate and the timing when the alkylation occurs in the topoisomerase II cleavage and resealing cycle have previously been determined (Kwok and Hurley, 1998). The topoisomerase II-induced alkylation of DNA by psorospermin occurs at a time preceding the topoisomerase II-mediated strand cleavage event because it occurs in the absence of $Mg^{2+}$. The alkylation of DNA by psorospermin takes place at N7 of guanine in the presence of topoisomerase II since substitution of the target guanine by 7-deazaguanine prevents alkylation.

Because the stimulation of the topoisomerase II-induced DNA cleavage by psorospermin can be slowly reversed by the addition of excess salt, this indicates that alkylation of DNA by psorospermin traps a reversible topoisomerase II-DNA complex. It is believed that it is the psorospermin-DNA adducts, not the abasic sites resulting from depurination, that are responsible for the stimulation of the topoisomerase II-mediated cleavage. Since the precise location of the psorospermin within the topoisomerase II cleavage site is known, together with the covalent DNA linkage chemistry and the conformation of the psorospermin-DNA adduct, this structural insight provides a guide for the design and synthesis of new, more effective topoisomerase II poisons.

Psorospermin has a number of intrinsic features that have apparent advantages over existing topoisomerase II poisons or sequence-specific alkylators. First, psorospermin is a covalent topoisomerase II poison and will accordingly have an infinite "dwell time" at the topoisomerase II gate in comparison to doxorubicin or mitoxanthone. Second, because of the topoisomerase II site-directed alkylation, psorospermin has much greater sequence selectivity than comparable alkylating agents. Third, as is described next, there is evidence of down regulation of overexpressed oncogenes in cancer cells treated with psorospermin and psorospermin analogs.

IV. Down Regulation of Oncogenes by Psorospermin

A. Use of Topoisomerase II to Site-Direct the Alkylation of Overexpressed Oncogenes It is believed that topoisomerase II α and β will be able to site-direct the drug alkylation of different oncogenes, which depend upon the precise steric and electronic characteristics of the psorospermin analogs. Since topoisomerase II plays a role in site-directing the alkylation in transcriptionally active regions, it is important to ascertain the role of topoisomerase II in transcription. In principle, the transcriptional complex can rotate around the DNA, thus negating the need for topoisomerases to prevent the buildup of supercoiling in front of the RNA polymerase. However, it is clear that the lack of topoisomerases slows transcription (Brill et al., 1987a,b; Schultz et al., 1992), and in the absence of topoisomerases, transient supercoiling occurs (Liu and Wang, 1987).

These observations support the idea that topoisomerase II can direct the alkylation of psorospermin at transcriptionally active regions. This idea, coupled with the premise that steric and electronic features of the topoisomerase II poison can affect the precise sequences for the site-directed alkylation, suggests that it is possible to select compounds from a library of psorospermin analogs that will target transcriptionally active genes such as oncogenes (BMI-1, BCL-2, c-jun, c-myc) that are actively overexpressed in cancer cells. The selection of psorospermin analogs that are not only topoisomerase II poisons but will also down-regulate downstream oncogenes that are anti-apoptotic dramatically increases the potential value of the selected compounds as clinically effective compounds active in drug-resistant tumors.

Particularly, it is believed that psorospermin analogs may be used to down regulate BMI-1. BMI-1 is a putative oncogene belonging to the Polycomb group family, and is found in leukemias, lymphomas, and some solid tumors. The BMI gene has been located on chromosome 10p13, a region involved in chromosomal translocations in infant leukemias and rearrangements in malignant T cell lymphomas (Bea et al., 2001). It is believed that an agent that down regulates BMI-1 results in an increase in c-myc induced apoptosis.

A two-step approach may be taken to determining which psorospermin analogs target oncogenes. First, the effect of steric and electronic interactions at various sites on the peripheral parts of the xanthone can be determined. These sites are limited, but will reveal where peripheral functionalization is possible. Second, different intercalating species and peripheral substituents can be tested. These latter species may be chosen based upon the results of the first step.

B. Promoter Assays for Various Oncogenes

Selected oncogenes may be examined in separate promoter assays. DNA chip array technology may also be used to scan a multitude of oncogenes. Various oncogenes can be assayed against a selected psorospermin analog to determine the ability of the analog to regulate the oncogene. The selection of psorospermin analogs that are not only topoisomerase II poisons, but that also will down-regulate oncogenes that are anti-apoptotic, enhances the potential of these compounds to be clinically effective antitumor agents.

Various cloning strategies for oncogene reporter assays will be apparent to those skilled in the art. One method is to use the commercially available pGL2 luciferase reporter vector (Promega). The fragment and vector DNA may be digested with restriction enzymes that will generate compatible ends for cloning. In most cases, the ends of the DNA fragment may require modification, either by using synthetic linkers, by a PCR reaction using primers containing sites for appropriate restriction enzymes, or by filling in the restriction site overhang. It is advantageous to treat the vector DNA with calf intestinal phosphatase to remove 5' phosphate groups, thus preventing reclosure of the vector on itself without an insert.

Sufficient DNA may be prepared to perform control reactions for digestion, ligation, and transformation steps. To ensure capture of the correct insert DNA, the desired restric tion fragment may be purified by electrophoresis on an acrylamide or agarose gel and then recovered from the gel by one of several methods, such as using the Wizard™ PCR Preps DNA Purification System. Alternatively, unfractionated restriction fragments can be cloned into the target plasmid, and the desired recombinant can then be identified by gel electrophoresis of plasmid DNA.

Transfection of DNA into eukaryotic cells may be mediated by cationic liposomes (e.g., Transfectam® Reagent) (Schenborn and Goiffon, 1991), calcium phosphate (Cullen, 1987; Ausubel et al., 1988), DEAE-dextran (Cullen, 1987; Rosenthal, 1987), or electroporation (Ausubel et al., 1988). Firefly luciferase may be assayed by measurement of light production upon addition of luciferin and ATP. Generally, these assays are very rapid and sensitive. (de Wet et al., 1987; Wood, 1990). The promoter fragments from the genes of interest can be generated by PCR with primers derived from the genomic DNA sequence. PCR reactions may be run with Pfu DNA polymerase (Stratagene) for 25 amplification cycles. The products can then be cut with appropriate restriction enzymes and then subcloned into pGL-2-Basic vector (Promega).

For instance, the specific down regulation of BMI-1 in lymphoma cells has been demonstrated. Another oncogene of interest is BCL-2. Human BCL-2 displays a complex gene structure and an equally complex strategy for expression. There are two separate promoter regions that are retained during the t(14;18)(q32;q21) translocation, which occurs in over 80% of follicular non-Hodgkin's lymphomas (Yunis et al., 1982; Levine et al., 1985). The results of the translocation are deregulation of the BCL-2-Ig allele, while the normal BCL-2 gene is transcriptionally silent. The $P_2$ promoter in the BCL-2-Ig fusion gene is immediately 5' to the open reading frame (ORF) in exon II and is a classic TATA plus CAAT box, and as expected, two distinct initiation sites can be found. The second promoter ($P_1$) exists 5' to exon I. This promoter contains 7 Sp1 binding sites but no TATA box. The BCL-2 antisense used so successfully in clinical trails (Webb, 1997) is targeted at the ORF of the BCL-2 mRNA and leads to down-regulation and apoptosis. The adjacent $P_2$ promoter may be used as a target for topoisomerase II-directed alkylation by psorospermin analogs.

C. Cytotoxicity Evaluations of Select Psorospermin Analogs

Prior to further evaluation in vitro to examine effects of selected analogs of psorospermin on gene expression and determination of the location of topoisomerase II site-directed alkylation in oncogenes, it may be desirable to conduct in vitro cytotoxicity assays in appropriate matched pairs of cell lines. For example, it analogs are identified that down-regulate BCL-2, matched pairs of lymphoma lines may be used, one with normal and the second with overexpressed of BCL-2, to look for differential drug sensitivity. The methods for drug treatment, cultivation, and determination of cytotoxic potency are discussed further herein.

D. Determination of the Effects of Selected Compounds on Differential Gene Expression Patterns and the Location of Topoisomerase II Site-Directed Alkylations Following identification of select compounds that down-regulate defined oncogenes, these compounds may be examined using the gene chip arrays to look for patterns of gene expression that will confirm the primary role of damage to the promoter that leads to the observed effect. For example, compounds that interact with the $P_1$-promoter of c-myc to down-regulate this gene have previously been identified. DNA chip array analysis showed that other genes that are controlled by c-myc, such as h-TERT, ODC, and CDC 25A, are also down-regulated following c-myc down-regulation.

If the use of promoter assays to identify compounds that down-regulate selected oncogenes is not successful, gene chip arrays may be used as a primary screen. Compounds may be selected that have promising activity based upon in vitro cytotoxicity in select pairs of cell lines (e.g., sensitivity in a cell line that is known to overexpress a particular oncogene).

Once it has been determined through the promoter and DNA microarray analysis that a critical oncogene expression is down-regulated in target cells after administration of the psorospermin analog, LM-PCR may be used to determine the precise sequence site for alkylation. In this assay, transient transfection in HeLa cells is carried out followed by psorospermin analog treatment. After isolation of the plasmid DNA containing the target promoter (e.g., BCL-2), the DNA breaks at the position of an alkylated base or restriction enzyme site are converted to blunt ends by denaturing the substrate DNA followed by primer extension. Blunt ligation of an asymmetric linker followed by nested PCR and labeled primer extension yields a band of known length on a sequencing gel.

This assay is ideally suited for evaluating DNA damage in a plasmid that has been transfected into tissue culture cells. For these experiments, a plasmid with the BCL-2 promoter and a suitable restriction enzyme site introduced just upstream of the promoter sequences may be used. After digestion and piperidine cleavage, LM-PCR may be used to determine the relative amount of topoisomerase II site-directed DNA alkylation.

V. Evaluation of Psorospermin Analogs in Cell-Free and In Vitro Systems

A. Target Cancers

Those skilled in the art will realize that the psorospermin analogs of the present invention may be used to treat a variety of cancers. Two cancers of particular importance, lymphomas and leukemias are discussed here.

(i) Low-grade non-Hodgkin's lymphomas. The most common mechanism for resistance of non-Hodgkin's lymphomas is overexpression of the BCL-2 gene, which results in resistance to programmed cell death (apoptosis), leading to chemoresistance (Miyashita and Reed, 1992). In fact, a prognostic marker of low-grade, follicular non-Hodgkin's lymphoma is overexpression of BCL-2 (Hermine et al., 1996; Hill et al., 1996). In a pivotal study (Webb et al., 1997) antisense oligonucleotides targeted at the open reading frame of BCL-2 mRNA caused a specific down-regulation of BCL-2 expression, which led to tumor regression in patients.

For example, in the treatment of non-Hodgkin's lymphoma in a phase I trial in relapsed patients with BCL-2-positive lymphomas, disease stabilization was seen in 43% of patients and improvements were seen in 14%. A phase-II study in combination with cytotoxics is now in progress, alongside other studies involving patients with relapsed small-cell lung carcinoma, breast, colorectal, hormone-resistant metastatic colorectal cancer, and relapsed acute leukemia (Waters et al., 2000). Thus, therapies directed at BCL-2 go well beyond lymphomas as potential tumor targets.

Because topoisomerase II directs the alkylation of psorospermin, and BCL-2 mRNA expression is activated in non-Hodgkin's lymphoma cells, it is desirable to identify psorospermin analogs that will alkylate oncogenes in addition to producing a topoisomerase II poisoning effect. In this way, the topoisomerase II poisoning effect will be more likely to induce apoptosis in target cells in the absence of the anti-apoptotic effect of overexpressed oncogenes. As a further measure to increase selectivity, the psorospermin analogs may be combined with CPT-11 as a topoisomerase I poison, which elevates topoisomerase II levels.

(ii) Leukemias. One of the important contributors to drug refractory leukemias is resistance to topoisomerase II poisons. Resistance to topoisomerase II-targeted drugs is multifactorial and includes drug membrane transporters, downstream events, cell cycle regulation, and down-regulation of topoisomerase II expression (Dingemans et al., 1998). In addition, the target topoisomerase II can contribute to this resistance, which results in ineffective interactions at the topoisomerase II gate site. This may result from reversibility of the ternary complex, which, in the case of intercalators such as doxorubicin and mixanthone, leads to free drug and undamaged DNA before the poisoned effect leads to induction of apoptosis.

Psorospermin has several advantages over these noncovalent topoisomerase II inhibitors. First, the reversal of topoisomerase II from the ternary complex still leaves an alkylated guanine. Second, the dwell time of psorospermin is essentially infinite within the ternary complex because of the covalent adduct. Third, the intercalation site of psorospermin is between +1 and +2 of the topoisomerase II gate, as opposed to the clinically used topoisomerase II poisons, which are between −1 and +1, and therefore mutant topoisomerase II enzymes. These mutant enzymes resist ternary complex formation or reverse easily, and should still be sensitive to psorospermin. One or more of these rationales may explain the documented sensitivity of drug-resistant leukemias to psorospermin.

In addition to the rationale described above, the overexpression of BCL-2 and c-jun in leukemias provides an additional strategy similar to that described for BCL-2-overexpressing lymphomas. This may also be a useful strategy for obtaining psorospermin analogs active in drug refractory leukemias.

Leukemia cell lines may be used to test whether the combined use of CPT-11 and psorospermin will increase the sensitivity of cancer cells to psorospermin. In L1210 leukemia-bearing mice, the different scheduling of the topoisomerase I and topoisomerase II poisons camptothecin and teniposide can give rise to either antagonism or synergy (Eckard et al., 1993; Hammond et al., 1998). Simultaneous administration gives rise to antagonism, whereas sequential administration to the topoisomerase I and then the topoisomerase II poisons gives rise to synergy. The apparent explanation is that cells treated with topoisomerase I poisons compensate by up-regulating topoisomerase II levels. Cells with increased levels of topoisomerase II become supersensitive to topoisomerase II poisons.

VI. Preparation of Psorospermin and Psorospermin Analogs

The present invention discloses several methods for synthesizing psorospermin analogs, including optically active analogs, with the following formula:

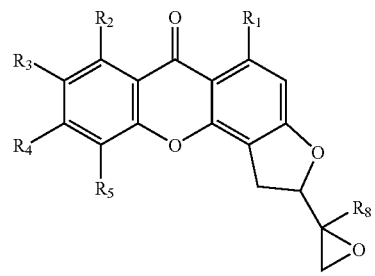

wherein $R_1$ is H, OH, O-alkyl, $OCH_3$, halogen, or alkyl; $R_2$-$R_4$, is H, OH, O-alkyl, $OCH_3$, halogen, or alkyl; $R_5$ is H, O-alkyl, or alkyl; and $R_8$ is H or alkyl. These psorospermin analogs can be synthesized by a reaction scheme utilizing a new Wacker type cyclization reaction. The cyclization reaction is illustrated in scheme 1.

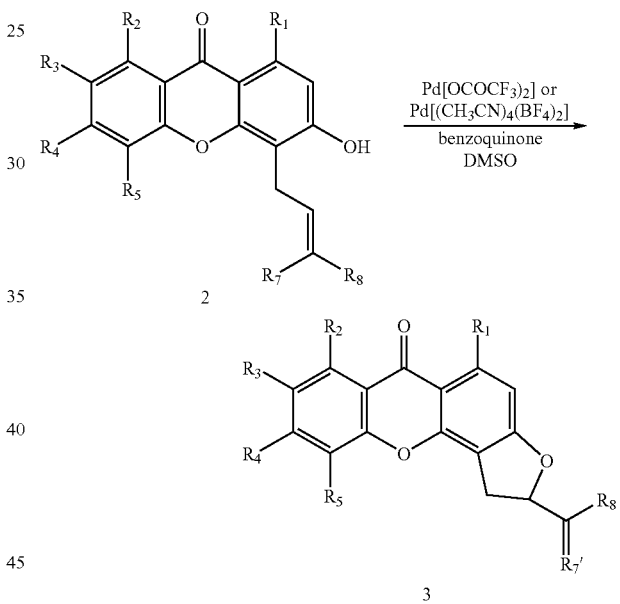

Psorospermin analogs (1) can be formed from (3) by performing an epoxidation or an epoxide forming reaction.

A. Synthesis of Racemic Psorospermin Analogs

Approaches to the synthesis of (±)-(2'R,3'R) psorospermin (4) have been investigated by two different groups of chemists. In order to determine the absolute stereochemistry of (4), Cassady and coworkers completed a total synthesis of the diastereomeric $O^5$-methyl-(±)-(2'R,3'S) psorospermin (Cassady et al., 1987a). Later, they constructed the dihydrobenzofuran portion of (4) using asymmetric epoxidation and the zip-type sequence developed by Nicolaou as the key steps (Cassady et al., 1987b).

Although these studies are extremely insightful, they do not allow for analogs to be synthesized at a late stage of the synthesis because of the method used to install the sensitive epoxide group. Kupchan and Streelman (1977) were able to synthesize $O^5$-methyl-(±)-(2'R,3'R) psorospermin, based on an olefinic intermediate; however, their synthesis does not address the optical activity of (4), and the overall yield was poor due to a low yield of the key step. The method of the present invention utilizes an asymmetric Wacker-type cyclization shown to form new benzofuran intermediate (5) with the desired olefin substitution (Hayashi et al., 1999). These chiral olefinic products may then be manipulated into many desired analogs prior to installing the labile epoxide.

A retrosynthetic analysis of (4) according to one embodiment of the present invention is shown in Scheme 2.

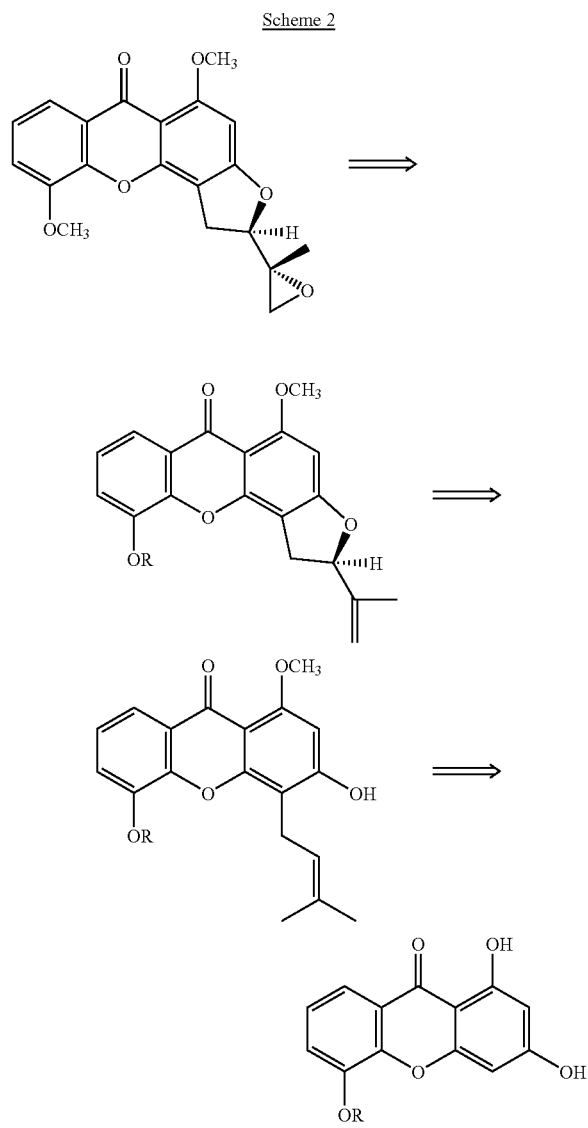

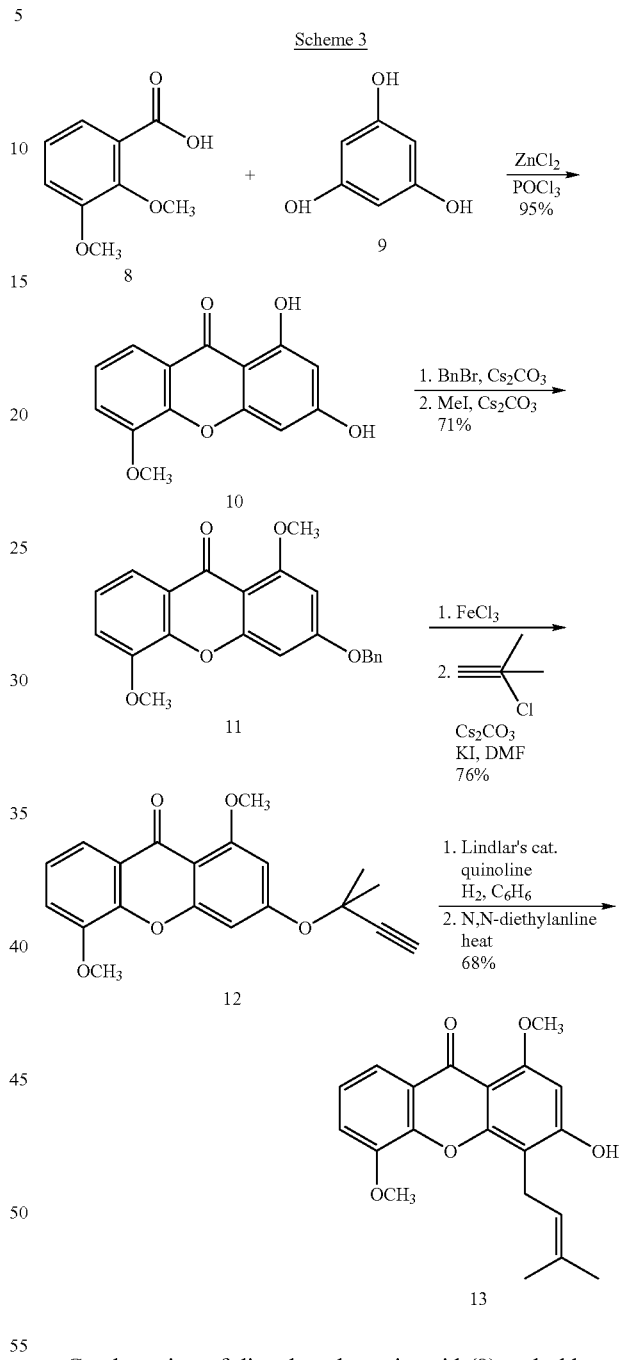

Psorospermin analogues may be obtained through the introduction of the epoxide via asymmetric dihydroxylation of olefin (5). The key intermediate (5) may be synthesized from the allylphenol (6) through a new Wacker-type cyclization. The cyclization precursor (6) may be made from the xanthone (7) after claisen rearrangement and a short series of protecting group manipulations.

Those skilled in the art will realize that this method may be used to make a variety of psorospermin analogs. One such analog is $O^5$-methyl-(±)-(2'R,3'R) psorospermin (16) (Hurley and Fellows, 2000). The allylphenol (13) was synthesized, upon which the Wacker cyclization could be tested. One method of synthesis is shown in scheme 3.

Condensation of dimethoxybenzoic acid (8) and phloroglucinol (9) provided xanthone (10) (Grover et al., 1955; 1956). Selective alkylation of the phenol which is not chelated to the ketone with benzyl bromide followed by alkylation with MeI provided (11) (Cassady et al., 1987a). Debenzylation with $FeCl_3$ followed by alkylation with propargyl chloride afforded alkyne (12). Reduction to the olefin with Lindlar's catalyst followed by Claisen rearrangement afforded the substrate (13) for Wacker cyclization (Taylor et al., 1969, 1971; Hlubucek et al., 1969).

Wacker cyclization of (13) in DMSO afforded a 69% yield of furan (14), as shown in scheme 4.

Scheme 4

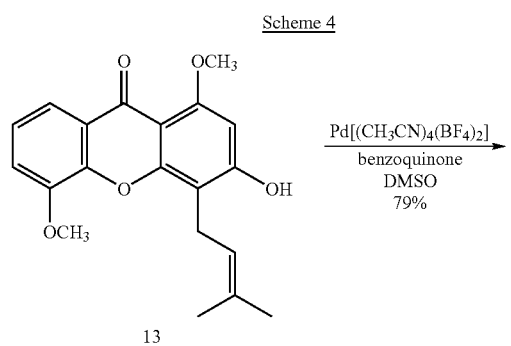

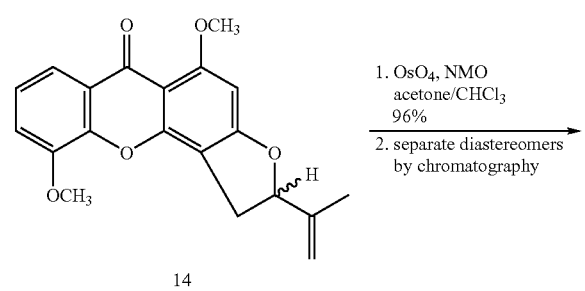

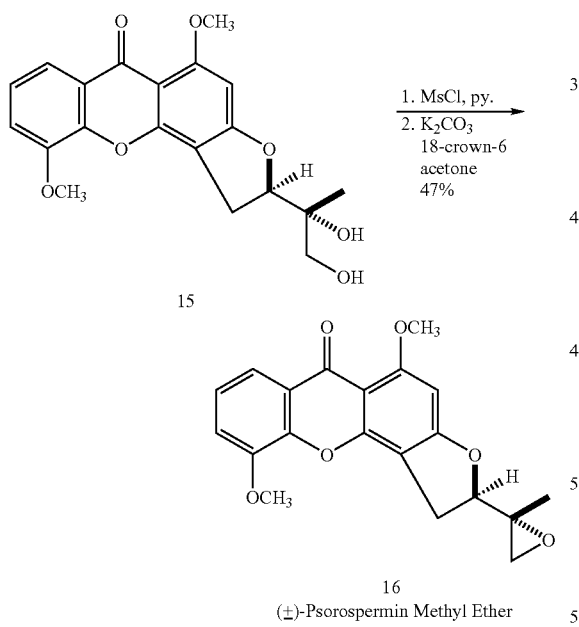

16
(±)-Psorospermin Methyl Ether

It will be readily apparent to those skilled in the art that reagents other than those shown in the reactions shown herein may also be used. For instance, in the Wacker cyclization step, Pd(OCOCF$_3$) may be used in place of Pd((CH$_3$CN)$_4$(BF$_4$)$_2$).

Comparison of the optical rotation of the synthesized methyl psorospermin to that obtained from the methylated natural product, revealed that there had been no asymmetric induction (Kupchan and Streelman, 1977). The reaction was conducted without chiral ligand and found to produce racemic (14) in excellent yield. Dihydroxylation of olefin (14) under standard conditions provided the diastereomeric diols (15), which could be separated by chromatography. Mesylation of (15) followed by treatment of the crude mesylate with K$_2$CO$_3$ and 18-crown-6 in acetone provided the final epoxide O$^5$-methyl-(±)-(2'R,3'R) psorospermin (16).

One synthetic route according to the present invention for (±) psorospermin methyl ether is shown in scheme 5.

Scheme 5

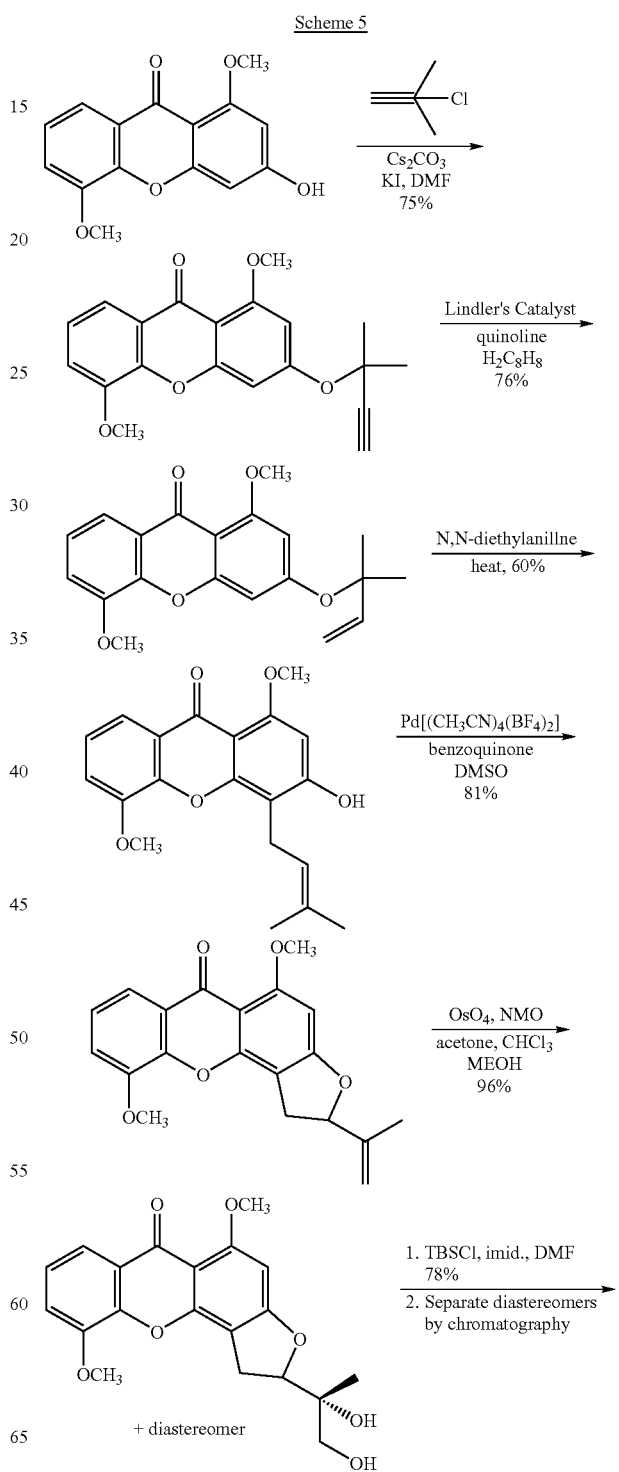

-continued

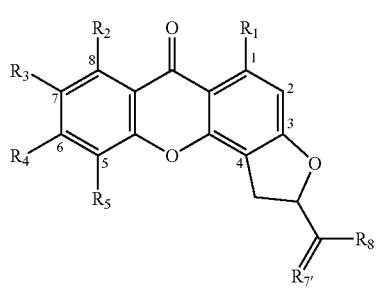

TBAF, THF →

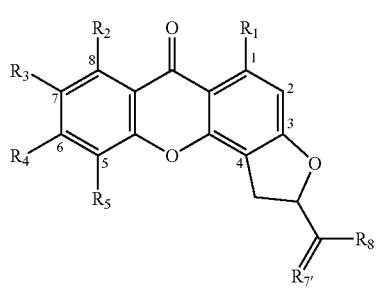

1. MsCl, py.
2. $K_2CO_3$
18 crown-6
acetone
47%
(3 steps)

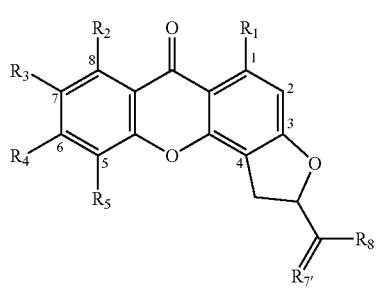

A variety of other psorospermin analogs can be synthesized using this reaction scheme by simply varying the starting materials to obtain psorospermin products with desired ligand groups at various locations on the psorospermin analog. For instance, substitution of different compounds for (8) and (9) can be used to produce a xanthone starting material with ligands at various positions on the xanthone compound. By using different starting materials, the methods of the present invention can be used to produce an intermediate having a formula:

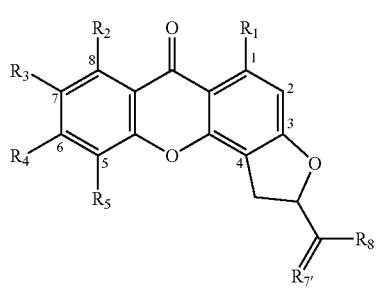

where $R_1$-$R_5$, $R_7$, and $R_8$ are independently hydrogen, a phenyl, an alkyl, a hydroxyl, a hydroxyalkyl, a halogen, an amine, an alkylamine, a thiol, or an alkylthiol. As well as psorospermin analogs having a formula:

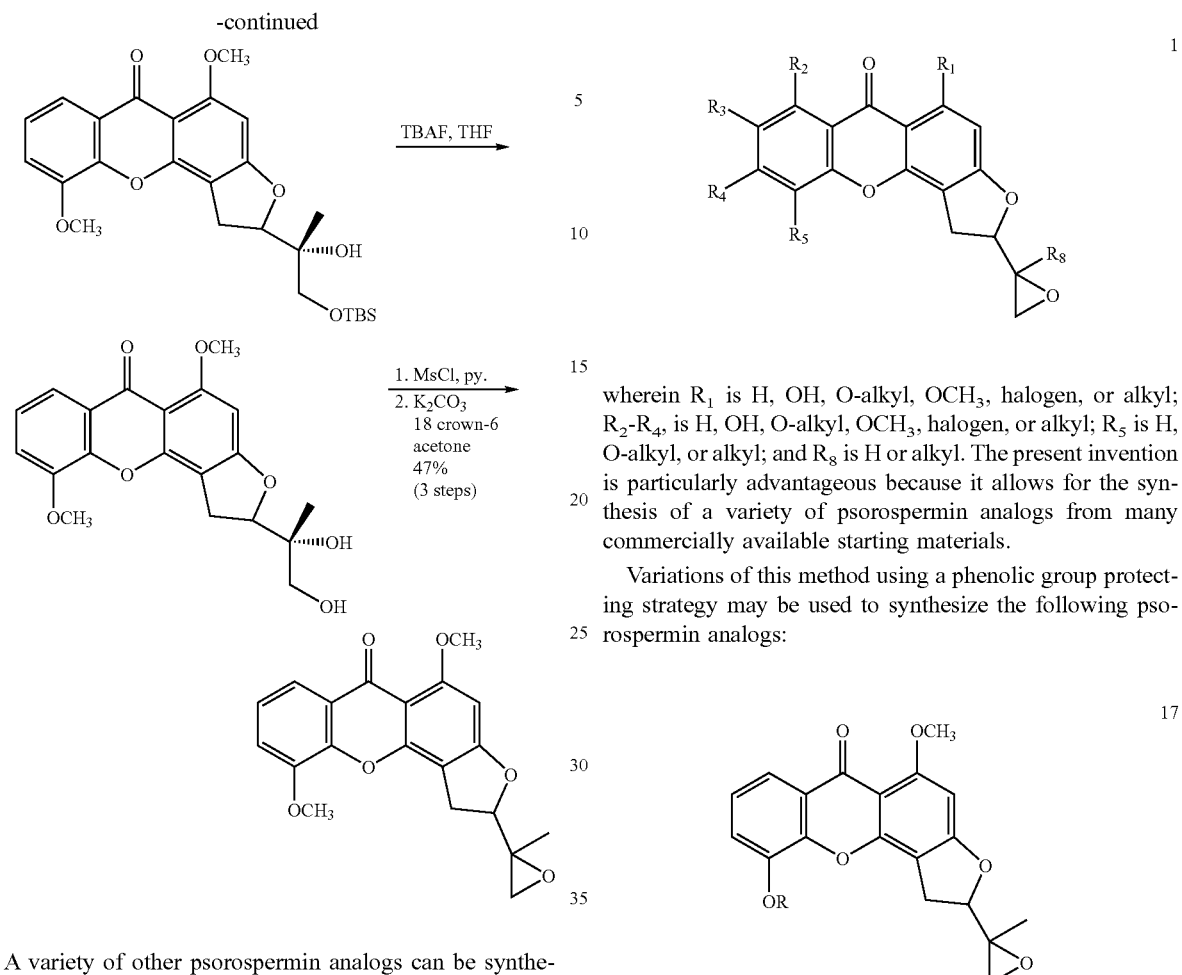

wherein $R_1$ is H, OH, O-alkyl, $OCH_3$, halogen, or alkyl; $R_2$-$R_4$, is H, OH, O-alkyl, $OCH_3$, halogen, or alkyl; $R_5$ is H, O-alkyl, or alkyl; and $R_8$ is H or alkyl. The present invention is particularly advantageous because it allows for the synthesis of a variety of psorospermin analogs from many commercially available starting materials.

Variations of this method using a phenolic group protecting strategy may be used to synthesize the following psorospermin analogs:

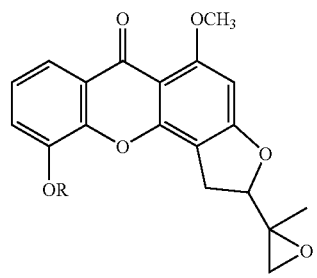

where R is an alkyl, a hydroxyl, a hydroxyalkyl, a halogen, a benzyl, an amine, an alkylamine, a thiol, or an alkylthiol. Compounds (17) may be synthesized from a compound having the following formula:

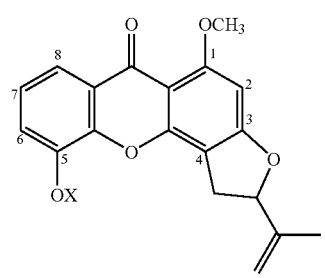

where X is a protecting group. A preferred protecting group is tert-butyl silane, although other suitable protecting groups may also be used.

Compound (19) may be made using the Wacker cyclization reaction previously described. A preferred method of synthesizing compound (19) in which the protecting group is TBS is illustrated in scheme 6.

Scheme 6

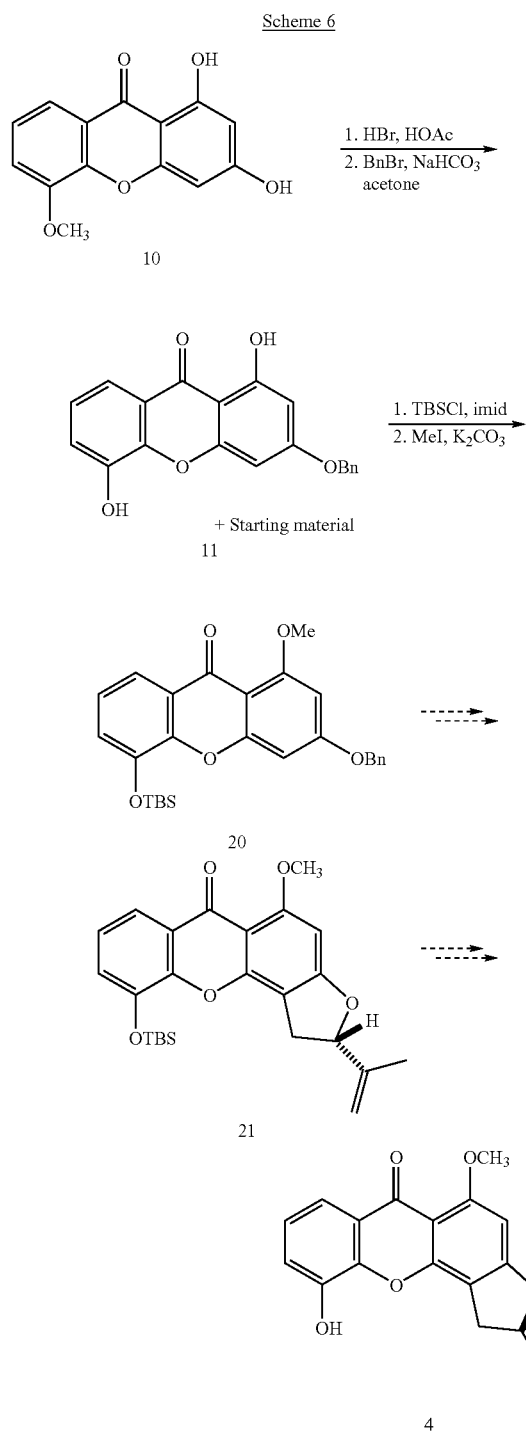

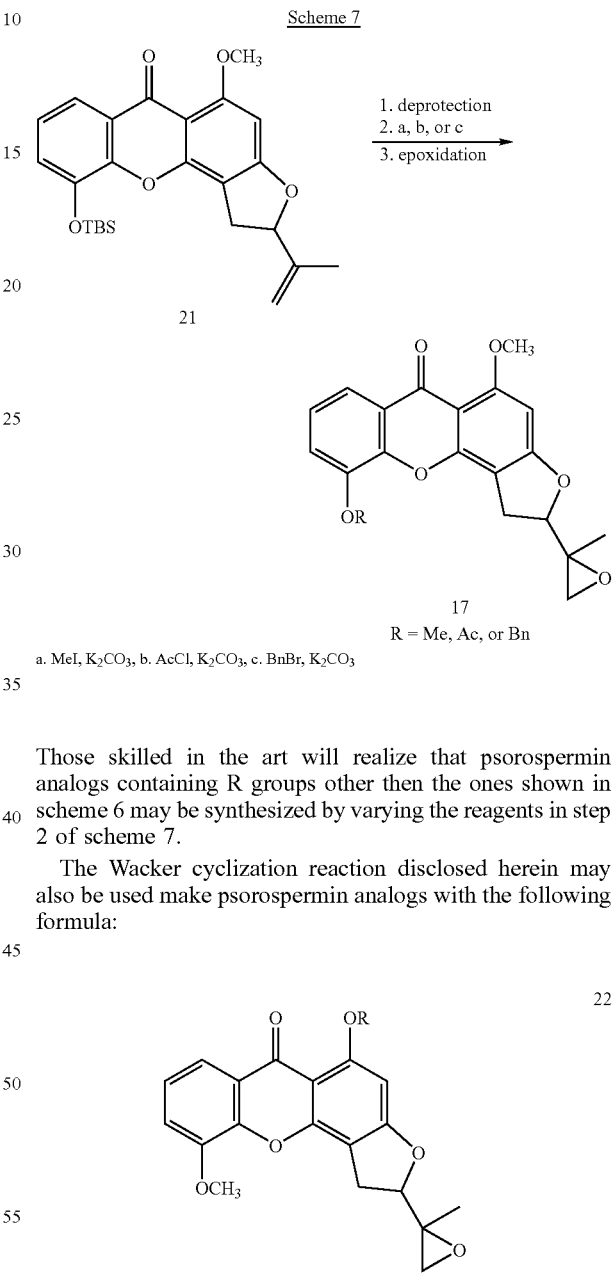

Scheme 7

R = Me, Ac, or Bn
a. MeI, K₂CO₃, b. AcCl, K₂CO₃, c. BnBr, K₂CO₃

Compound (17) may be synthesized by performing a deprotection reaction on compound (19) to remove the protecting group, placing a desired ligand group on the oxygen located at the 5' position of compound, and carrying out an epoxidation or epoxide performing reaction. A preferred synthetic method for producing various analogs of compounds (17) is shown in scheme 7.

Those skilled in the art will realize that psorospermin analogs containing R groups other then the ones shown in scheme 6 may be synthesized by varying the reagents in step 2 of scheme 7.

The Wacker cyclization reaction disclosed herein may also be used make psorospermin analogs with the following formula:

where R is hydrogen, an alkyl, a hydroxyl, a hydroxyalkyl, a halogen, a benzyl, an amine, an alkylamine, a thiol, or an alkylthiol. These analogs may be synthesized by removing the CH₃ group from the 1' position of compound (5), reacting the resultant product with an alkylating agent and a base, and then carrying out an epoxidation or epoxide forming reaction. One method for forming several analogs of compound (22) is shown in scheme 8.

Cleavage of the methyl ether (10) under acidic conditions followed by selective alkylation with benzyl bromide provides (11). Silyl ether protection followed by methylation affords (20). Next, benzyl ether (20) may be converted to the substrate for Wacker cyclization through the same reaction steps used on the model substrate in scheme 3. Analogously, cyclization should provide the olefinic xanthofuran (21), which can be further manipulated to afford various psorospermin analogs.

Scheme 8

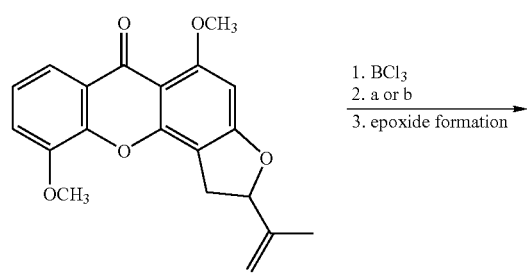

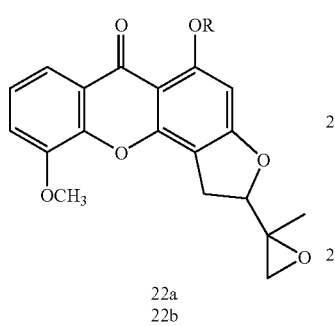

a. EtI, $Cs_2CO_3$, b. Isopropyl bromide, KI, $Cs_2CO_3$

B. Synthesis of Optically Active Psorospermin Analogs

A variation of the previously disclosed method may also be used to form optically active psorospermin analogs. Specifically, an asymmetric dihydroxylation of the intermediate (3) can be performed to yield a third compound having (+) and (−) diastereomers. The (−) diastereomers may then be isolated, preferably by chromatography. An epoxidation or epoxide forming reaction may then be done to yield a (−) psorospermin analog product. A variety of reagents can be used to perform the asymmetric dihydroxylation reaction, preferred agents include: 1) tBu-OH, $CH_3CN$, $H_2O$, $OsO_4$, and a chiral ligand, 2) a chiral ligand, $K_3Fe(CN)_6$, $K_2CO_3$, and $K_2OsO_4 \cdot 2\,H_2O$, 3) tBu-OH, $CHCl_3$, $H_2O$, $OsO_4$, and chiral ligand or 4) a chiral ligand, $K_3Fe(CN)_6$, $K_2CO_3$, and $K_2OsO_4 \cdot 2\,H_2O$.

One example of this method is illustrated in scheme 9.

Scheme 9

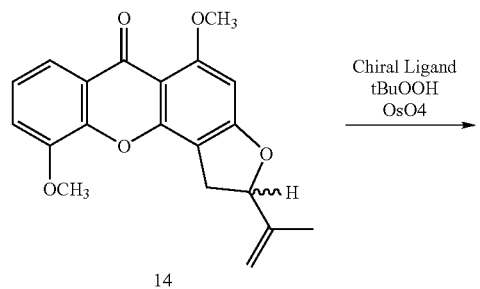

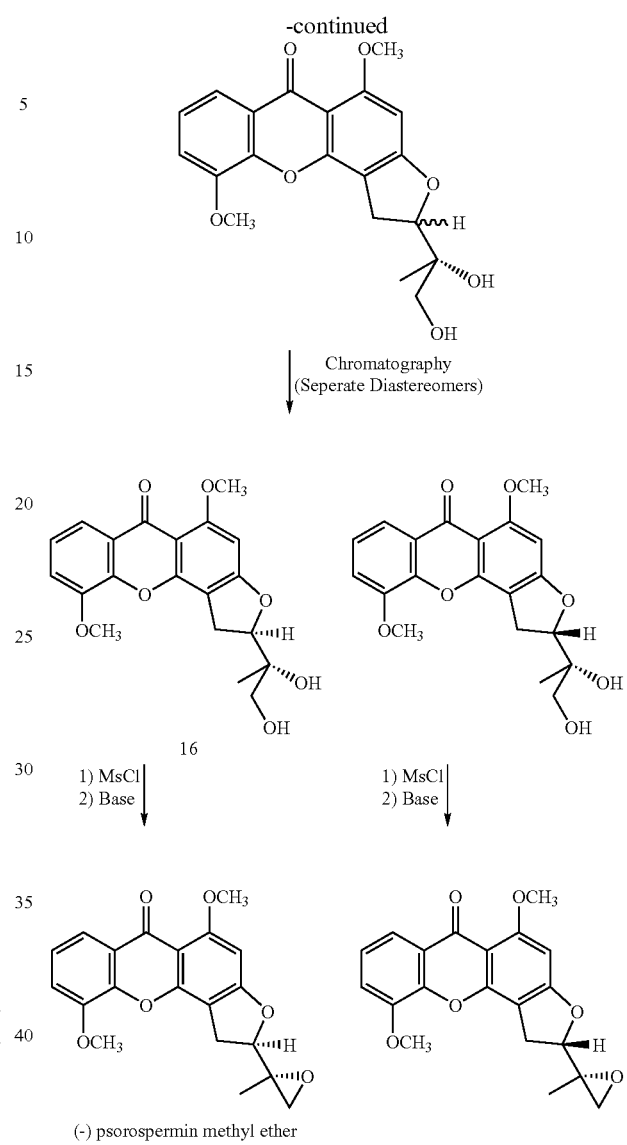

(−) psorospermin methyl ether

Optically active (−) psorospermin analogs may also be prepared using a method similar to that shown in scheme 4. After obtaining a compound with a formula:

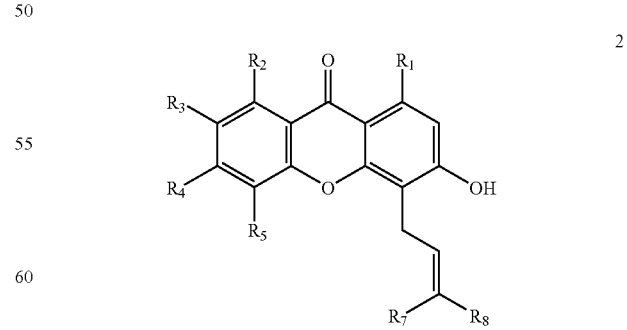

$R_1$-$R_5$ and $R_7$-$R_8$ are independently hydrogen, a phenyl, an alkyl, a hydroxyl, a hydroxyalkyl, a halogen, an amine, an alkylamine, a thiol, or an alkylthiol, a Wacker cyclization reaction similar to the one previously described is performed, but a chiral ligand is also used. One preferred embodiment comprises reacting compound (2) with Pd((CH₃CN)₄(BF₄)₂) or Pd(OCOCF₃)₂, a chiral ligand, and benzoquinone in DMSO. The remaining steps of scheme 4 may then be performed to obtain a (−) psorospermin analog.

Preferred chiral ligands for use in this reaction include ip-boxax, bisoxaxoline binapthyl, or spiro-bis(isoxazoline). Other suitable ligands will be apparent to those skilled in the art.

C. Development of Parallel Synthesis in Solution Phase to Generate Psorospermin Analogs (−)-Rotenone is commercially available and relatively inexpensive (Aldrich, Inc.), and most importantly it contains the same (2R)-benzodihydrofuran as psorospermin. Because of these characteristics, it was selected as the starting material for synthesizing psorospermin analog (26). The initial synthesis was carried out as shown in Scheme 10A.

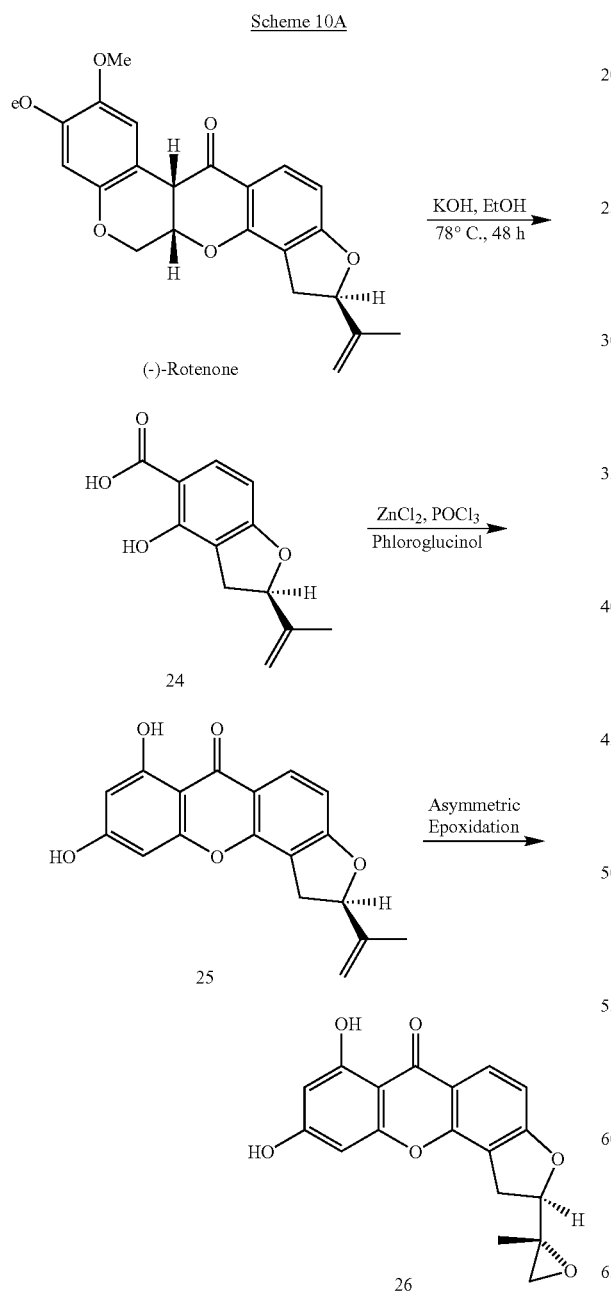

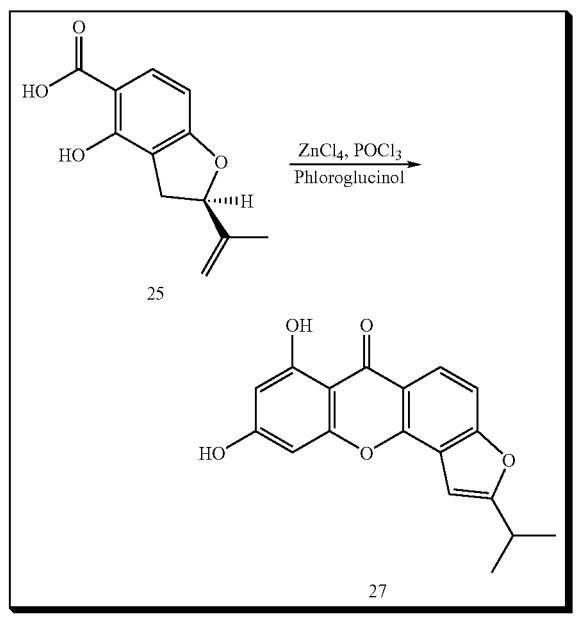

Instead of giving the desired xanthone (25), the Grover, Shah, and Shah condensation of tubaic acid (24) with phloroglucinol gave compound (27), (Ahluwalia and Tehim, 1984; Locksley et al., 1971), in which the double bond migrated. Moreover, various attempts to achieve the condensation reaction under different conditions were frustrated due to the sensitivity of the allylic ether moiety to reagents with Lewis acids.

In order to overcome this problem, a strategy of pro-functionalized double bond may be adopted. For two reasons the intermediate 1,2-diol (29) is selected as a bridge equivalent to accomplish the purpose as shown in scheme 11.

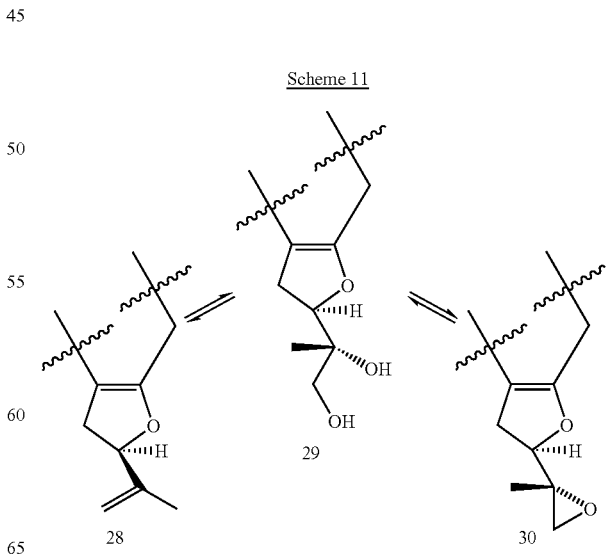

First, it can be made easily from olefin (28) with enantiopurity, and second, it can be directly stereospecifically converted to epoxide (30). Consequently, a new synthetic plan is outlined in scheme 12.

Scheme 12

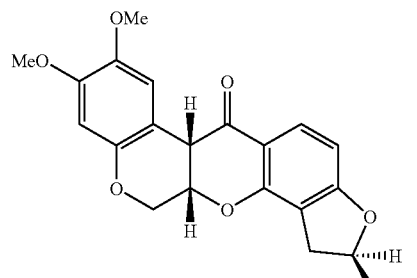

(−)-Rotenone 24

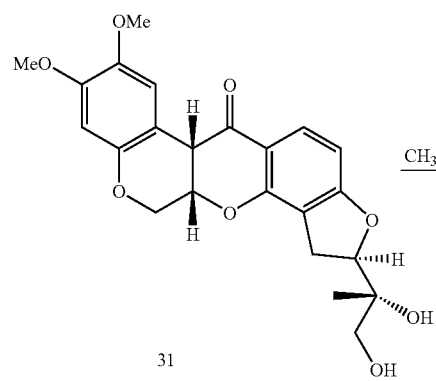

31

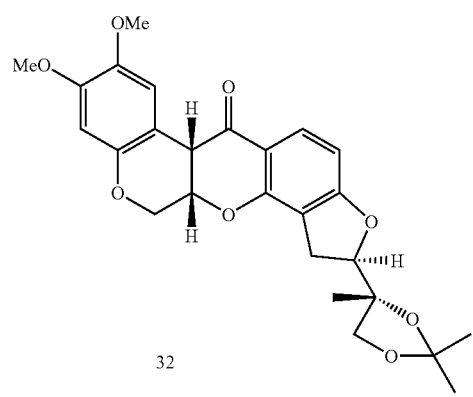

32

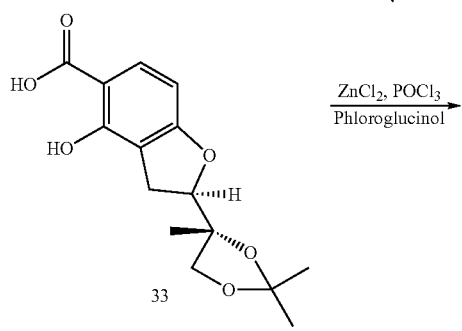

33

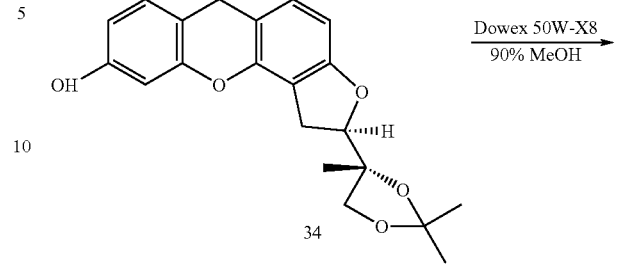

34

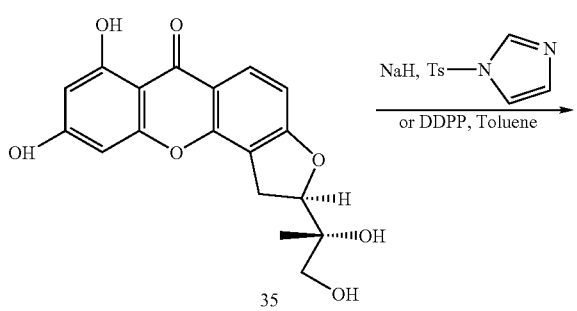

35

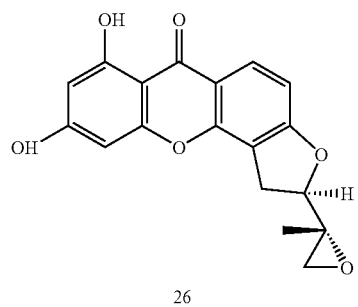

26

Sharpless asymmetric dihydroxylation of (−)-Rotenone gives the chiral diol (31) (Sharpless et al., 1992; Kolb et al., 1994). Protection of diol (31) with 2,2-dimethoxypropane affords 1,2-acetonide (32) (Kitamura et al., 1984). Oxidative degradation of compound (32) gives the o-hydroxy benzoic acid (33) (Cockerill et al, 1995). $ZnCl_2$-mediated condensation of o-hydroxy benzoic acid (33) with phloroglucinol is expected to generate the desired xanthone (34) (Ahluwalia and Tehim, 1984; Locksley et al., 1971; Dean, 1973). Deprotection of xanthone (34) with Dowex 50W-X8 (Park et al., 1994), followed by cyclodehydration with NaH and 1-(p-toluenesulfonyl)imidazole (Ireland and Smith, 1988) or polymer-$P(OEt)_2Ph_2$ in toluene (Kelly et al., 1985), completes the synthesis of psorospermin analog (26).

Not only does this synthetic route take just six concise steps to prepare psorospermin analog (26), but it also paves the way to a convergent approach to synthesize psorospermin analogs by coupling component A with component B in three steps, as illustrated in the preparation of psorospermin analog (26) from compound (33) in Scheme 12 and Table 3.

TABLE 3
Structure of Psorospermin Analogs in Library
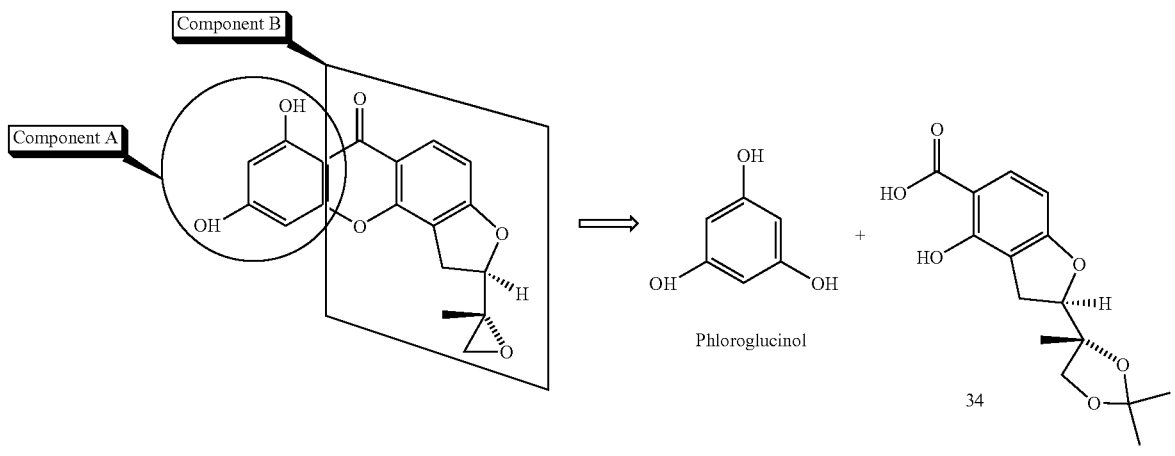
Component A
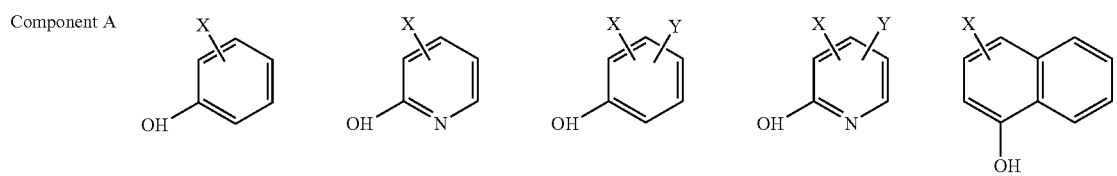
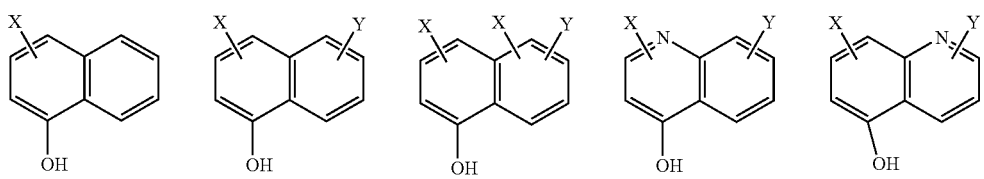
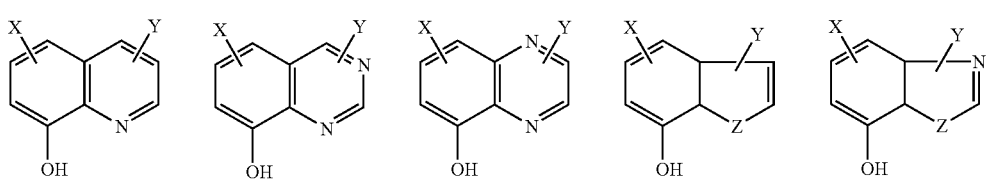
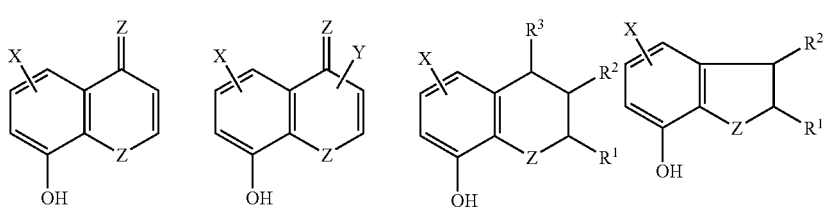
X, Y = H, OH, OR, SH, SR, SOR, SO$_2$R, Cl, Br, F, NHCOR, COR, CO$_2$R, NO$_2$,
1°, 2°, 3° Alkyl, Allyl, Benzyl; Z = O, S, NR.

TABLE 3-continued

Structure of Psorospermin Analogs in Library

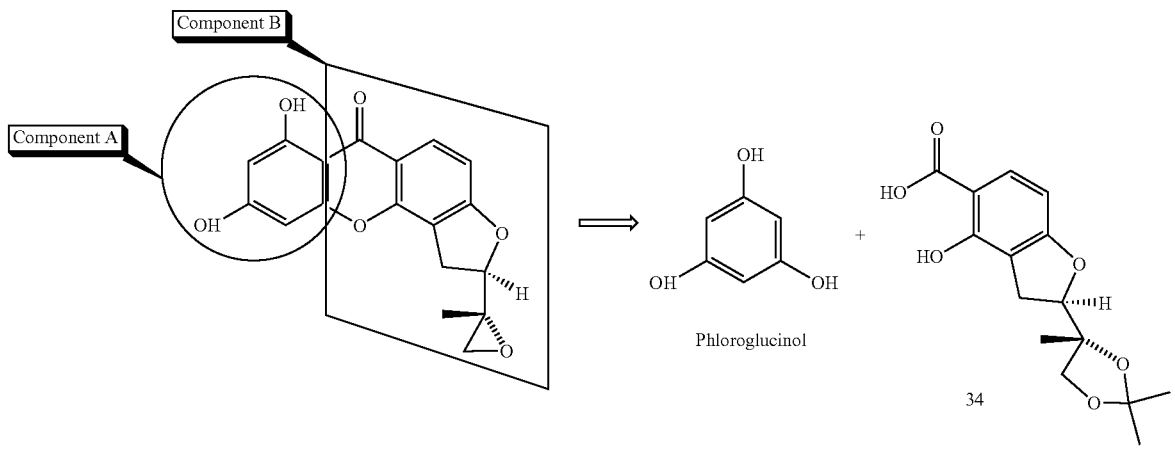

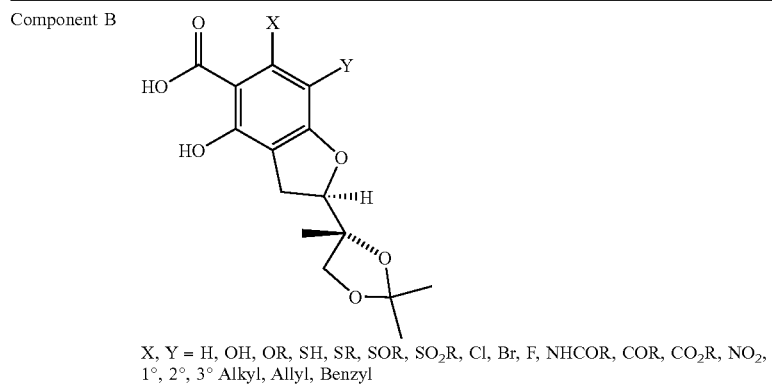

X, Y = H, OH, OR, SH, SR, SOR, $SO_2R$, Cl, Br, F, NHCOR, COR, $CO_2R$, $NO_2$, 1°, 2°, 3° Alkyl, Allyl, Benzyl This approach provides an attractive opportunity to synthesize molecularly diverse psorospermin analogs. A focused psorospermin library may be constructed in the parallel solution synthesis, since two of three reactions can use polymer-supported reagents, as indicated in scheme 12. The representative structures of components A and B inputted into the library are shown in Table 3. The psorospermin analogs can be synthesized, screened, and analyzed in an iterative manner. The results of SAR at the end of each cycle will provide the direct information for designing and synthesizing additional psorospermnin analogs, thereby avoiding synthesizing unnecessary psorospermin analogs, reducing cost and time. This strategy will allow the fullest representative diversity of psorospermin analogs to be synthesized with minimum resources. Furthermore, evaluation of these compounds can identify potential drug candidates. Furthermore, Each of the diasteromers from formula 1 can also undergo a further separation by chiral chromatography to yield optically pure enantomers. Typically a chiral stationary phase such as Pirkle chiral stationary phases, Davankov chiral stationary phases or Cyclodextrin bonded phases are used in either normal or reverse phase chromatography. One embodiment of this method separates either diasteromer of the psorospermin methyl ether into optically pure enatiomers using a stationary phase of 3,5-dinitroaniline derivatized (s)-tert-leucine bound to silica gel with a mobile phase of hexane, 1,2-dichloroethane and isopropanol as in Scheme 10B.

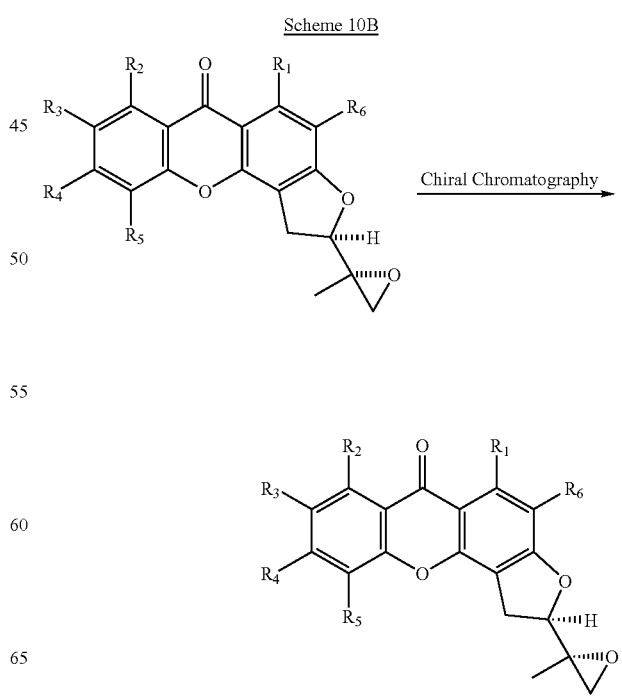

Scheme 10B

Chiral Chromatography

VII. Selection of Pharmaceutically Effective Psorospermin Analogs

The design of pharmaceutically effective new psorospennin analogs is guided by two observations. First, the selectivity of psorospermin for alkylation of DNA is dependent upon the presence of topoisomerase II. Background alkylation of duplex DNA in the absence of topoisomerase II is poor and shows little, if any, sequence selectivity. (Hansen et al., 1996). Thus, it is the level of topoisomerase II that determines the alkylation frequency in the target cell. It is therefore undesirable to design and synthesize psorospermin analogs that lose this topoisomerase II-dependent reactivity. Consequently, analogs of psorospermin that have excessive stabilizing interactions with duplex DNA and produce inherently high levels of reactivity with naked DNA are undesirable for biological use.

Second, while a structure of the psorospennin-DNA duplex adduct has been obtained, based upon NMR and molecular modeling, the real receptor in the cell is the topoisomerase II-DNA complex. The psorospermin binding pocket on the DNA is likely to be similar for both the binary (drug-DNA) and ternary (drug-topoisomerase-DNA) complexes, but in the absence of a structure of the ternary complex, it is not known what the critical interactions are between psorospermin and topoisomerase II. These are highly likely to occur because the drug traps the topoisomerase II-DNA adduct in some sequences. However, this is only one of the four possible consequences, as shown in FIG. 5.

The compilation of a library of biologically effective psorospermin analogs can be achieved by initially making modest substitutions on the aromatic ring that should not adversely affect duplex DNA reactivity, but may effect interactions with the topoisomerase II-DNA complex. It is suspected that these may modulate the outcomes shown in FIG. 5, e.g., catalytic inhibition, topoisomerase II poisoning, site-directed alkylation of DNA, and abasic site formation. Modulation or attenuation of these outcomes is important because this is likely to affect the overall efficacy of the drug in different target cells. For example, one cancer cell line may be more susceptible to the topoisomerase II site-directed alkylation near a transcriptionally active region or a replication fork than a different cell line that has higher topoisomerase II and is therefore more susceptible to topoisomerase II poisoning effects.

While modeling of the psorospermin-DNA adduct and the various psorospermin analogs may not provide significant insight into the interactions with topoisomerase II, it does provide some insight into the DNA interactions. For instance, the benzofuran and epoxide portions of the analogs shown in Table 4 do not show much variability from one minimized structure to another, but the modeling is useful in predicting interactions with the flanking base pairs. Thus, there are possible H-bonding interactions that result from phenolic substituents at C6 and C8.

Molecular modeling, superimposition of energy minimized conformation, and docking the ligand molecule of psorospermin and its analogs on the DNA were carried out using SYBYL and adjusted in MIDAS. Molecular modeling of psorospermin analogs was carried out mainly to view the position of the psorospermin analog with respect to the DNA, to determine the intermolecular hydrogen bonds, and to measure the potential energy of the complex. These results were compared with the psorospermin modeling data to support the rationale for the design of new psorospermin analogs. All the analogs form stable interactions with $d(ACGT)_2$ and stack the aromatic chromophore in an orientation parallel to the adjoining base pairs, and they also position the reactive epoxide into proximity of N7 of guanine similar to psorospermin. As revealed by the superimposition of the energy-minimized analogs with psorospermin, all psorospermin analogs shown in Table 4 retain conformation and stereochemistry similar to psorospermin.

For example, psorospermin analogs having the following formula:

with OH and OCH₃ substitution at R₁ and/or R₃ position, shown in Table 4, position these substituents in proximity to the minor groove. A number of existing topoisomerase II inhibitors are also known to intercalate DNA and contain substituents that bind to the minor groove (Cummings et al., 1996). Structure-activity studies of a series of intoplicine analogs show the importance of the hydroxyl group of the intercalators for topoisomerase inhibition (Nabiev et al., 1994). Elevated topoisomerase II inhibition by compounds containing additional hydroxy groups in key positions has been observed for mitoxanthone analogs (De et al., 1993).

TABLE 4

Structure of proposed psorospermin analogs.

| | 1 | 2 | 3 | 4 | 5 | 6 | 7 | 8 | 9 |
|---|---|---|---|---|---|---|---|---|---|
| $R_1$ | OH | OH | OCH₃ | OH | OH | OCH₃ | OH | OH | OCH₃ |
| $R_2$ | OH | OCH₃ | OCH₃ | OH | OCH₃ | OCH₃ | OH | OCH₃ | OCH₃ |
| $R_3$ | H | H | H | OCH₃ | OCH₃ | OCH₃ | OH | OH | OH |

VIII. Therapies

A. Cancers

The psorospermin analogs of the present invention may be used to treat a variety of cancers. These include, for example, pancreatic cancer, prostate cancer, leukemias, lymphomas, myelomas, ovarian cancer cell, and breast cancer. The psorospermin analogs may also be used to treat multi-drug resistant (MDR) cancer cells, including MDR cancer cells that are resistant to topoisomerase II inhibitors and MDR cancer cells mediated by MRP-1 or glycoprotein.

B. Pharmaceutical Preparations

Pharmaceutical compositions of the present invention comprise an effective amount of one or more psorospermin analogs or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one psorospermin analog or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The psorospermin analogs may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The psorospermin analogs may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the psorospermin analogs are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

C. Combination Therapies

In order to increase the effectiveness of the psorospermin analogs, it may be desirable to combine these compositions and methods of the invention with an agent effective in the treatment of hyperproliferative disease, such as, for example, an anti-cancer agent. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

More generally, such an agent would be provided in a combined amount with one or more psorospermin analogs effective to kill or inhibit proliferation of a cancer cell. This process may involve contacting the cell(s) with an agent(s) and the psorospermin analog at the same time or within a period of time wherein separate administration of the psorospermin analog and an agent to a cell, tissue or organism produces a desired therapeutic benefit. This may be achieved by contacting the cell, tissue or organism with a single composition or pharmacological formulation that includes both a psorospermin analog and one or more agents, or by contacting the cell with two or more distinct compositions or formulations, wherein one composition includes a psorospermin analog and the other includes one or more agents.

The terms "contacted" and "exposed," when applied to a cell, tissue or organism, are used herein to describe the process by which a therapeutic construct a psorospermin analog and/or another agent, such as for example a chemotherapeutic or radiotherapeutic agent, are delivered to a target cell, tissue or organism or are placed in direct juxtaposition with the target cell, tissue or organism. To achieve cell killing or stasis, the psorospermin analog and/or additional agent(s) are delivered to one or more cells in a combined amount effective to kill the cell(s) or prevent them from dividing.

The psorospermin analog may precede, be co-current with and/or follow the other agent(s) by intervals ranging from minutes to weeks. In embodiments where the psorospermin analog, and other agent(s) are applied separately to a cell, tissue or organism, one would generally ensure that a significant period of time did not expire between the time of each delivery, such that the psorospermin analog and agent(s) would still be able to exert an advantageously combined effect on the cell, tissue or organism. For example, in such instances, it is contemplated that one may contact the cell, tissue or organism with two, three, four or more modalities substantially simultaneously (e.g., within less than about a minute) as the psorospermin analog. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the psorospermin analogs.

Various combination regimens of the psorospermin analogs and one or more agents may be employed. Non-limiting examples of such combinations are shown below, wherein a composition the psorospermin analogs is "A" and an agent is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of the composition of the psorospermin analogs to a cell, tissue or organism may follow general protocols for the administration of chemotherapeutics, taking into account the toxicity, if any. It is expected that the treatment cycles would be repeated as necessary. In particular embodiments, it is contemplated that various additional agents may be applied in any combination with the present invention.

1 Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with Ad-mda7 gene therapy. The general approach for combined therapy is discussed below. Generally, the tumor cell must bear some marker that is amenable to targeting, e.g., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

4. Genes

In yet another embodiment, the secondary treatment is gene therapy in which a therapeutic polynucleotide is administered before, after, or at the same time as the psorospermin analog. A variety of proteins may be encompassed, some of which are described below.

a. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

b. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles.

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation. Since the $p16^{INK4}$ protein is a CDK4 inhibitor, deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p16^B$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines. Restoration of wild-type $p16^{INK4}$ function by transfection with a plasmid expression vector reduced colony formation by some human cancer cell lines.

Other genes that may be employed include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf erb, fms, trk, ret, gsp, hst, abl, E1A, p300, genes involved in angiogenesis (e.g., VEGF, FGF, thrombospondin, BAI-1, GDAIF, or their receptors) and MCC.

c. Regulators of Programmed Cell Death

Apoptosis, or programmed cell death, is an essential process for normal embryonic development, maintaining homeostasis in adult tissues, and suppressing carcinogenesis. The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli. The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $BCl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililies of the present invention by establishment of an autocrine or paracrine effect on hyperproliferative cells.

Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

IX. Biological Results

A. Comparative Cytotoxicity of Psorospermin and its Initial Restricted Group of Analogs in Select Cell Lines As an initial means of evaluating the potential of psorospermin and its analogs to demonstrate improved antitumor activity in vivo, select matched pairs of human cancer cell lines can be selected that will allow for the identification of analogs that may have improved activity because of defined properties, e.g., the ability to avoid drug resistance because of the presence of a mutant topoisomerase II, or the ability to down-regulate an overexpressed oncogene. Using these matched cell lines, a set of compounds can be evaluated for cytotoxic potency.

(i) Human tumor cell lines. Human tumor cell lines representative of major forms of human cancer for use in the microcytoxicity assay include MCF7 (breast), SW480 (colon), HL-60 (promyelocytic leukemia), MiaPaCa-2 (pancreatic), U937 (histiocytic lymphoma), and 8226 (myeloma) (see Table 5). One drug resistant variant of 8226 was also included: 8226/DOX40, an mdr-1-mediated drug resistant cell line. Other matched pairs may also be added. All lines have known karyotypes that are checked at least annually for quality control.

Cells were grown in suspension in RPMI 1640 medium supplemented with 5% fetal bovine serum, 1% (v/v) penicillin (100 unit/ml), streptomycin (100 µg/ml), and 1% (v/v) L-glutamine (all from GIBCO, Grand Island, N.Y.) at 37° C. in 5% $CO_2$, 95% air atmosphere, and were passaged once every six days. Additionally, these lines are capable of in vivo growth in SCID mice for in vivo confirmatory studies. In initial experiments, two diastereomeric pairs of (±)-psorospermin methyl ethers in a series of cell lines were evaluated. The results, shown in Table 5, show that as perhaps expected the diastereomeric pair consisting of (±)-(2'R,3'R) (2'S,3'S) psorospermin methyl ether ("Compound A"), which contains the natural enantiomeric psorospermin, is more potent than the "natural" (±)-(2'R,3'S) (2'S,3'R) psorospermin methyl ether ("Compound B").

TABLE 5

In vitro cytotoxic potency of
diastereomeric pairs of psorospermin methyl ethers.

| Cell lines | Compound A (µg/ml) | Compound B (µg/ml) |
|---|---|---|
| MCF7 | 0.28 | 0.74 |
| SW480 | 0.24 | 0.36 |
| MiaPaCa-2 | 0.26 | 0.48 |
| 8226 | 0.21 | 0.33 |
| 8226/DOX40 | 0.06 | 0.30 |
| U937 | 0.062 | Not determined |
| HL-60 | 0.026 | Not determined |

$IC_{50}$ values of (±)-(2'R,3'R)(2'S,3'S) psorospermin methyl ether in leukemias, lymphomas, and various solid tumors are shown in Table 6. $IC_{50}$ values for additional psorsopermin analogs are shown in FIG. 6.

TABLE 6

| Cell Line | Origin | $IC_{50}$ Values (µM) |
|---|---|---|
| HL60 | Multiple myeloma | 0.036 |
| HL60/AR (adriamycin resistant) | Acute promyelocytic leukemia | 0.012 |
|  | Acute promyelocytic leukemia | 0.011 |
| K562 | Chronic myelogenous leukemia | 0.036 |
| K562/R (daunorubicin resistant) | Chronic myelogenous leukemia | 0.024 |
| A2780 | Ovarian | 0.063 |
| A2780/CP70 (cisplatin resistant) | Ovarian | 0.473 |
| MCF7 | Breast, adenocarcinoma | 0.610 |
| MCF 10A | Breast, normal mammary | 5.350 |
| DU 145 | Prostate, brain mets | 0.304 |
| LnCAP | Prostate, lymph node mets | 0.460 |
| PEAZ-1 | Prostate, primary | 0.160 |
| PC-3 | Prostate, adenocarcinoma, mets | 0.280 |
| PC-3N | Prostate, N-cadherin positive | 0.130 |
| MIA PaCa-2 | pancreas | 0.180 |

Figure 8:
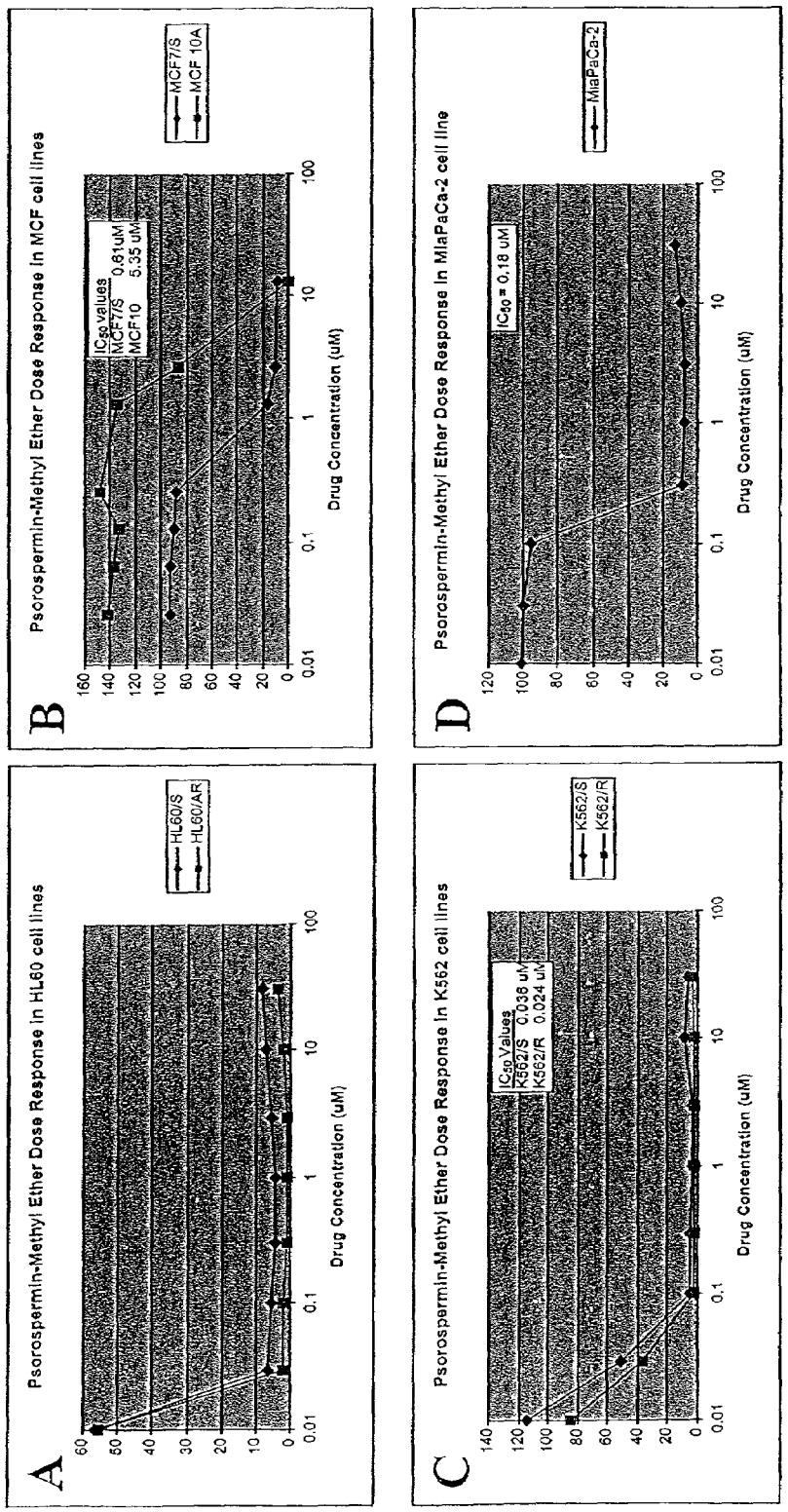
FIG. 8 shows examples of cytotoxicity of psorospermin methyl ether on matched leukemia and lymphoma cell lines, normal and neoplastic breast cells (MCF-7) and pancreatic cells (MiaPaCa).

A comparison of the sensitivity of matched cell lines to doxorubicin and psorospermin methyl ether is shown in FIG. 7, and examples cytotoxicity of psorospermin methyl ether on various cells lines is shown in FIG. 8.

TABLE 7

Effect of Optical Pure Enantiomer
Psorospermin Analogs in Tumor Cells
IC50 (nM)

| Compound | MiaPaCa | DU-145 | HT-29 |
|---|---|---|---|
| 116 | 4,000 | 4,000 | 7,000 |
| 117 | 400 | 400 | 700 |

The effect of optically pure (2S, 3R)-psorospermin methyl ether (116) and (2R, 3S)-psorospermin methyl ether (117) in tumor cells is shown in Table 7.

(ii) Microcytoxicity assay. A standard 96-well microcytoxicity assay is performed by plating each cell line in a microtiter plate at 4,000-10,000 cells per well (depending on cell doubling time), six replicate wells per drug dose. All plates are incubated for 4 days at 37° C. in a humidified tissue culture incubator containing 5% $CO_2$ in air. The endpoint determination uses sulforhodamine blue (SRB) and spectrophotometric determination of protein content of each well as reflected by SRB staining. $IC_{50}$ values were calculated by linear regression analysis.

(iii) Conclusion. Both compounds have a potent effect on all tumor cell lines tested. Compound A was, on average, twice as effective as compound B. HL-60 (acute promyelocytic leukemia, which is positive for c-myc and BCL-2) is highly sensitive to compound B. 8226 and 8226/DOX (myeloma cell lines in which mdr-1 is up-regulated (DOX) or BCL-2 is up-regulated (both)) show no mdr-1 resistance. Compound A shows a remarkable activity in the pancreatic cell line MiaPaCa, which is very difficult to treat. The activity in MiaPaCa is as good or better than with gemcytabine, the only approved drug for treatment of pancreatic cancer.

B. Differential Oncogene Expression Using DNA Chip Array Technology (i) Background. cDNA microarray analysis may be used to determine which genes or pathways are affected by treatment with a specific agent (psorospermin or analogs) or combination of agents (psorospermin and CTP-11). Hundreds of 5700 human gene chips have successfully been fabricated. This gene chip is composed of the first human gene set released by Research Genetics (97001.V), and consists of 5184 sequence-validated IMAGE consortium clones. Approximately 3000 are known genes and the remainder are "expressed sequence tags" (EST's), as determined by UniGene. Relevant information regarding each clone, such as accession number and Unigene cluster, can be obtained at the Research Genetics web site (www.resgen-.com). Each slide also contains a collection of "housekeeping" genes and nonhuman sequences to monitor sensitivity, fluorescent labeling efficiency, and nonspecific hybridization.

(ii) Data analysis. The results obtained by cDNA microarray analysis may be confirmed experimentally using standard RNA analysis techniques (e.g., Northern Blotting, RT PCR). In addition to the experimental confirmation, statistical approaches to assess the reproducibility of the results from the hybridizations may be used. The first test is based on the prediction that the vast majority of genes will not show differences in expression. By graphing the fluorescence intensities for each gene on separate axes, the genes without differences in expression will all fall on a line with a slope of 1.

To further assess the quality of the data, the consistency of the expression ratios measured across all three experiments may be calculated. The GenePix analysis software produces a median intensity value for each element of the microarray. The intensity and local background data from independent hybridizations may be normalized and used to calculate an average and standard deviation for each gene in each channel (Cy3 and Cy5). A significant difference in gene expression may be determined at the 90% confidence level by comparing the difference between the mean intensity in the two channels to 1.9 times the larger of the two channels' standard deviation. To determine a "true" background for the array results (local background does not account for nonspecific hybridization), the background subtracted signal intensity for 8 genes derived from Ice Plant (*Mesembryanthemum crystallinum*) was averaged and printed onto the microarray 16 times each to determine the standard deviation. Using these statistics data that represents the true signal at the 95% confidence level is selected (e.g., average Ice Plant signal +1.96 (SD Ice Plant signal)=low signal cut-off). An expression ratio is then calculated for the genes that have significant differences in expression and signal above "true" background in both channels.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Synthesis of Psorospermin Methyl Ether

A synthesis of psorospermin methyl ether is shown in scheme 13.

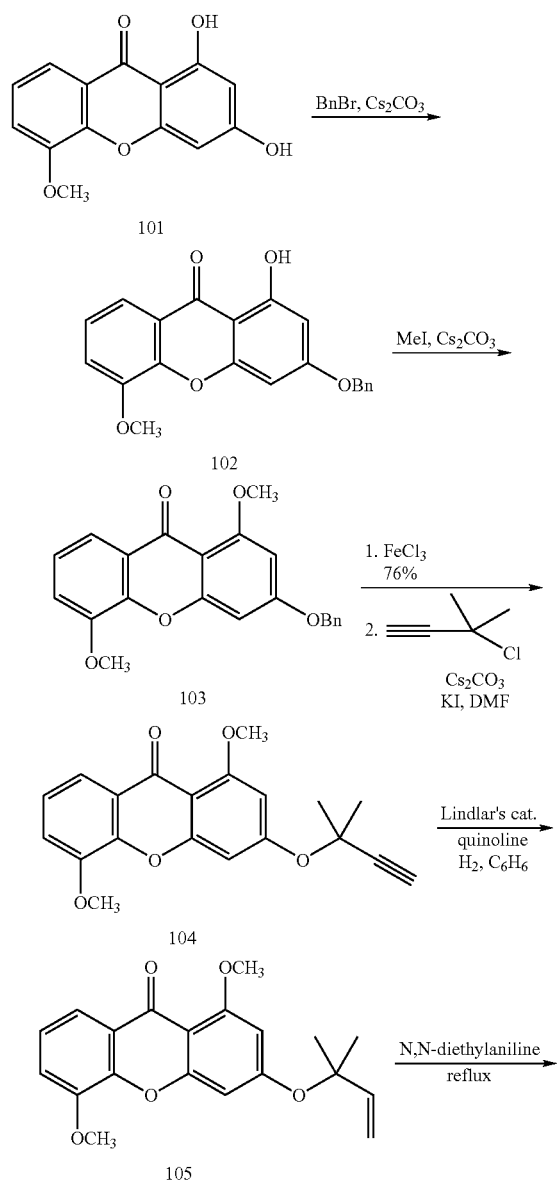

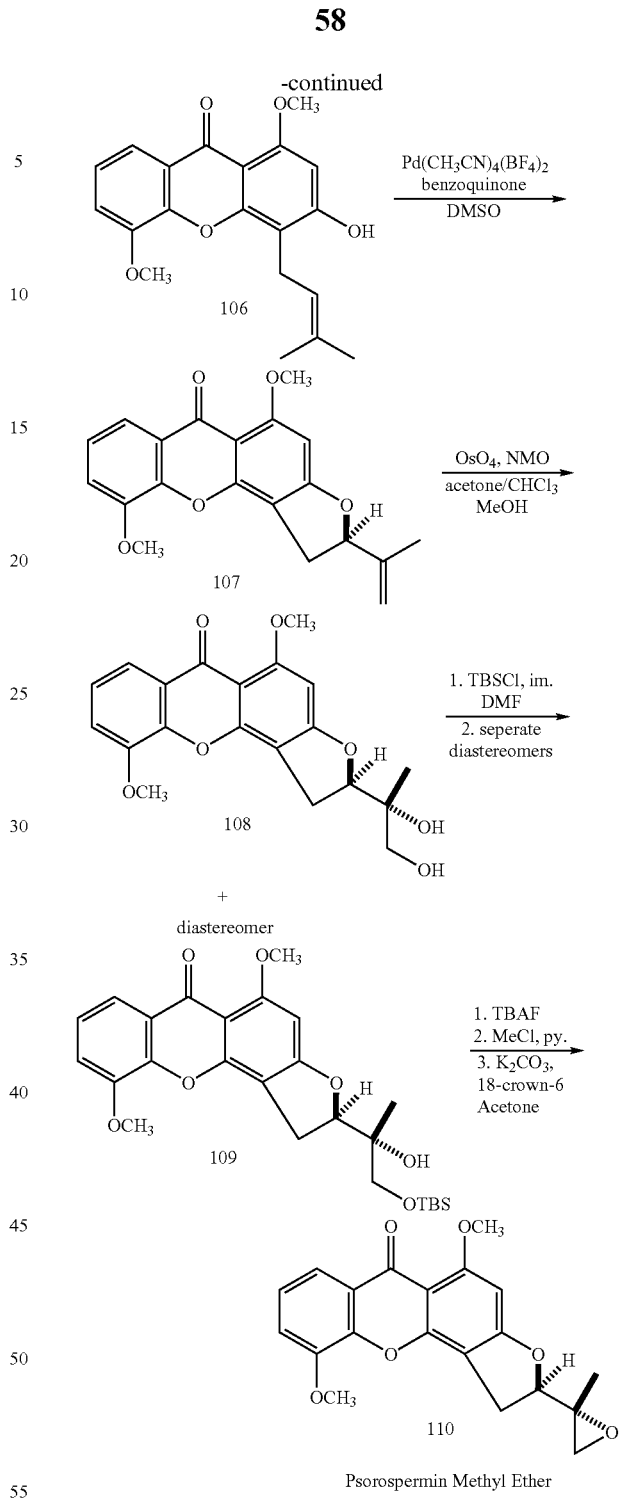

Psorospermin Methyl Ether

The following general procedures were followed. Unless otherwise noted, all starting materials were obtained from commercial suppliers and used without further purification. $Pd(CH_3CN)_4(BF_4)_2$ was obtained from Strem Chemicals. Dimethylformamide (DMF) and dimethylsulfoxide (DMSO) were purchased 99.8% anhydrous from Aldrich. Benzene was distilled from $CaH_2$. All reactions were run under an argon atmosphere unless noted. The $^1H$ and $^{13}C$ NMR spectra were determined, unless otherwise indicated, as solutions in $CDCl_3$ at the indicated field; chemical shifts are expressed in parts per million (δunits), referenced to the solvent. Splitting patterns are designated as s, singlet; d, doublet; t, triplet; app t, apparent triplet; q, quartet; m, multiplet; comp, complex multiplet; br, broad.

1,3-Dihydroxy-5-methoxy xanthone (101). Prepared according to the literature procedure of Cassady et. al. (1987a). All analytical data is satisfactory.

3-Benzyloxy-1-hydroxy-5-methoxy xanthone (102). $Cs_2CO_3$ (10.1 g, 31 mmol) was added in portions to phenol (101) (4.0 g, 15 mmol) and BnBr (1.7 ml, 14 mmol) in DMF (80 mL) at 0° C. The reaction was warmed to rt. After 5 h, phenol remains so more BnBr was added (0.1 mL) and the reaction stirred for 36 h (TLC: 40% EtOAC/hexane). The reaction was decanted and washed with $CH_2Cl_2$ into an erlenmeyer which had been placed in an ice cooled bath. With stirring, 2M HCl was added slowly until acidic by pH paper. After warming to rt, the reaction was diluted with $CH_2Cl_2$ (500 mL) and $H_2O$ (200 mL). The layers are separated and the aqueous layer was reextracted with $CH_2Cl_2$ (2×300 mL). The organic layers were combined, washed with brine (200 mL), dried ($Na_2SO_4$) and concentrated under reduced pressure to provide (3.9 g, 72%) of 2 as a pink solid. (LH-58-36) $^1H$ NMR (250 MHz, $CDCl_3$) δ 12.8 (s, 1H), 7.82 (d, 1H, J=5.9 Hz), 7.42-7.20 (complex, 7H), 6.64 (s, 1H), 5.30 (s, 2H), 4.03 (s, 3H); $^{13}C$ NMR (62.5 MHz) δ 180.1, 165.6, 163.1, 158.0, 147.0, 145.5, 135.6, 128.6, 128.2, 127.4, 123.4, 121.0, 116.5, 115.4, 104.2, 98.1, 93.3, 70.3, 56.2; mass spectrum (CI) m/z+1 349.1068 [$C_{21}H_{17}O_5$ (M+1) requires 349.1076] 349 (base), 259.

3-Benzyloxy-1,5-Dimethoxy xanthone (103). $Cs_2CO_3$ (27.0 g, 83 mmol) was added in portions to phenol (102) (14.5 g, 42 mmol) and MeI (8.0 mL, 125 mmol) in DMF (400 mL) at rt. After 3 h at 50° C., the reaction was decanted and washed with $CH_2Cl_2$ into an erlenmeyer which had been placed in an ice cooled bath. With stirring, 2M HCl was added slowly until acidic by pH paper. After warming to rt, the reaction was diluted with $CH_2Cl_2$ (800 mL) and $H_2O$ (400 mL). The layers are separated and the aqueous layer was reextracted with $CH_2Cl_2$ (300 mL). The organic layers were combined, washed with brine (400 mL), dried ($Na_2SO_4$) and concentrated under reduced pressure to provide a red sludge which could be tritrated with EtOH and filtered to afford (9.3 g, 66%) of (103) as a pink solid. Analytically pure material can be obtained at this point by column chromatography with 50% EtOH/hexane. (LH-63-5) $^1H$ NMR (250 MHz, $CDCl_3$) δ 7.84 (d, 1H, J=6.0Hz), 7.42–7.31 (complex, 5H), 7.20–7.07 (complex, 2 H), 6.63 (s, 1H), 6.37 (s, 1H), 5.08 (s, 2H), 3.92 (s, 3H), 3.88 (s, 3H); $^{13}C$ NMR (62.5 MHz) δ 175.2, 163.8, 161.7, 159.4, 147.8, 144.5, 135.6, 128.6, 128.3, 127.5, 123.9, 123.1, 117.5, 114.3, 106.1, 95.9, 93.6, 70.4, 56.3, 56.2; mass spectrum (CI) m/z+1 363.1242 [$C_{22}H_{19}O_5$ (M+1) requires 363.1232] 363 (base), 339.

1,5-Dimethoxy-3-(3'3'-dimethylpropynoxy) xanthone (104). $FeCl_3$ (9.0 g, 69 mmol) was added in portions to (103) (5.0 g, 17 mmol) in $CH_2Cl_2$ (150 mL). After stirring for 40 min, $H_2O$ was added (300 mL) and the reaction stirred/swirled vigorously. The reaction was filtered through a very large buchner funnel, and the brown ppt was washed with $H_2O$ (300 mL) and ether (200 mL) and dried overnight on the funnel.

To the crude dimethyl ether xanthone (3.27 g, 12.0 mmol) in DMF (60 mL) was added 3-chloro-3-methyl-1-butyne (11.8 g, 36.1 mmol), KI (1.0 g, 6.01 mmol) and $Cs_2CO_3$ (11.8 g, 36.1 mmol). The reaction was heated at 50° C. for 19 h, cooled to rt, and then placed in an ice-bath. 2M HCl was added until the reaction had been quenched and no more foaming was observed. The mixture was then diluted with $CH_2Cl_2$ (200 mL) and the layers were separated. The organic layer was washed with sat. NaCl (50 mL), dried ($Na_2SO_4$), and concentrated under reduced pressure. The crude product was purified by column chromatography (60% EtOAc/hex) to yield 3.50 g (75%) of a yellow solid. (LH-63-16) $^1H$ NMR (250 MHz, $CDCl_3$) δ 7.88 (d, 1H, J=5.12 Hz), 7.20-7.02 (m, 3H), 4.00 (s, 3H), 3.98 (s, 3H), 2.78 (s, 1H), 1.80 (s, 6H; $^{13}C$ NMR (62.5 MHz) δ 175.1, 161.4, 161.2, 158.7, 147.8, 145.2, 123.1, 117.6, 115.5, 114.5, 107.6, 98.7, 98.6, 84.6, 76.9, 72.6, 56.2, 29.4; mass spectrum (CI) m/z+1 339.1233 [$C_{20}H_{19}O_5$ (M+1) requires 339.1232] 339 (base), 273.

1,5-Dimethoxy-3-(3'3'-dimethylpropenoxy) xanthone (105). 5% Pd/$CaCO_3$ poisoned with lead (Lindlar's catalyst) (1.37 g, 0.642 mmol) was added to a solution of (104) (2.17 g, 6.42 mmol) and quinoline (3.5 mL) in benzene (200 mL). The reaction flask was evacuated, and then backfilled with $H_2$ from a balloon. The reaction was stirred under $H_2$ for 2 h. (The reaction can be monitored by the $^1HNMR$ of small aliquots which have been filtered through celite and concentrated, observing the disappearance of the alkyne proton or the appearance of the olefin protons.) After 2 h, more Pd catalyst was added (0.5 g) and the reaction was stirred 1.5 h more under $H_2$. The reaction was filtered through a pad of celite, washed with EtOAc (300 mL) and concentrated under reduced pressure. The residue was dissolved in $CH_2Cl_2$ (100 mL), washed with 2M HCl (4×200 mL) and sat. $NaHCO_3$, dried ($Na_2SO_4$), and concentrated under reduced pressure to yield 1.65 g (76%) of a yellow solid. (LH-63-17)

1H NMR (250 MHz, $CDCl_3$) δ 7.84 (d, 1 H, J=8.5 Hz), 7.25-7.11 (m, 2H), 6.71 (s, 1H), 6.38 (s, 1H), 6.16 (dd, 1H, J=17.7, 10.9Hz), 5.33-5.23 (comp, 2H), 3.99 (s, 3H), 3.93 (s, 3H), 1.54 (s, 6H); $^{13}C$ NMR (62.5 MHz) δ 176.4, 162.1, 161.0, 158.3, 148.0, 145.2, 143.3, 123.0, 117.5, 114.4, 114.3, 107.8, 98.7, 80.9, 56.2, 56.1, 27.2; mass spectrum (CI) m/z+1 341.1388 [$C_{20}H_{21}O_5$ (M+1) requires 341.1388] 339 (base), 273.

1,5-Dimethoxy-4-(1,1-dimethylpropene) xanthone (106). A suspension of (105) (0.23 g, 0.67 mmol) in diethylaniline (55 mL) was heated to 200° C. for 3 h, and cooled to rt. The reaction was filtered and the ppt. was washed with MeOH to provide 2.3 g (60%) of (106) as a beige solid. (LH-63-19).

$^1H$ NMR (250 MHz, DMSO-$d_6$) δ 10.8 (br s, 1H), 7.60-7.55 (d, 1H, J=7.8 Hz), 7.39-7.35 (m, 1H), 7.30-7.24 (m, 1H), 6.43 (s, 1H), 5.29-5.24 (m, 1H), 3.94 (s, 3H), 3.80 (s, 1H), 3.46-3.28 (comp, 2H); $^{13}C$ NMR (62.5 MHz) δ 174.2, 161.5, 159.7, 156.2, 148.4, 144.8, 131.1, 123.7, 123.3, 122.8, 116.7, 115.5, 107.7, 105.6, 95.6, 56.5, 56.4, 25.9, 21.9, 17.9; mass spectrum (CI) m/z+1 341.1389 [$C_{20}H_{21}O_5$ (M+1) requires 341.1389] 341(base).

(±) 1,5-Dimethoxy-2'-isopropenyl dihydrofuroanoxanthone (107). DMSO (118 mL) was added to a mixture of (106) (1.21 g, 3.56 mmol), Pd[($CH_3CN$)$_4BF_2$] (0.79 g, 1.78 mmol) and benzoquinone (recrystallized from EtOH, 3.84 g, 35.6 mmol). The solution was stirred 36 h, then poured into a separatory funnel containing $CH_2Cl_2$ (400 mL), and washed with $H_2O$ (2×300 mL). The layers were separated and the $H_2O$ layer was washed with $CH_2Cl_2$ (200 mL). The organic layers were combined and washed with sat. NaCl (200 mL), dried ($Na_2SO_4$) and concentrated under reduced pressure. The crude product was purified by column chromatography (50% EtOAc/hex), loading the product on the column in a minimum amount of $CH_2Cl_2$ to afford 0.15 g chromene (12%) and then 0.97 g (81%) of benzofuran (107) as a white solid. (LH-64-50).

$^1H$ NMR (250 MHz, $CDCl_3$) δ 7.82 (d, 1H, J=7.9 Hz), 7.25-7.06 (comp, 2H), 6.30 (s, 1H), 5.34 (app t, J=8.5 Hz), 5.08 (s, 1H), 4.92 (s, 1H), 3.93 (s, 3H), 3.91 (s,3H), 3.50 (dd, 1H, J=9.8, 15.4 Hz), 3.15 (dd, 1H, J=7.9, 15.4 Hz), 1.80 (s, 3H); $^{13}$C NMR (62.5 MHz) δ 175.0, 165.6, 162.9, 154.2, 147.8, 144.8, 143.0, 123.9, 123.0, 117.7, 114.5, 112.5, 106.7, 104.6, 89.7, 88.0, 56.4, 56.2, 31.2, 16.9 ; mass spectrum (CI) m/z+1 339.1232 [$C_{20}H_{19}O_5$ (M+1) requires 339.1236] 339 (base).

(2R*',3R*')-1,5-Dimethoxy-3',4'-dihydroxy dihydrofuranoxanthone (108). A solution of (107) (0.25 g, 0.74 mmol) in CHCl$_3$ (2.5 mL) was added to N-methyl morpholine oxide (NMO) (0.10 g, 0.89 mmol) and OsO$_4$ in 1:1H$_2$O/acetone (2 mL). The reaction was stirred 2 h, until no starting material remained by TLC (EtOAc). TLC shows two diastereomers, the lower Rf, being the desired diastereomer (108A). The reaction was filtered and the ppt. was washed with H$_2$O (5 mL) and acetone (2 mL), and collected to yield a diastereomeric mixture of (±) (108) (0.24 g, 96%). $^1$H NMR analysis shows a 2:1 mixture of diastereomers (B:A). (LH-64-37). $^1$H NMR 8A (250 MHz, DMSO-d$_6$) δ 7.61 (d, 1H), 7.40-7.25 (comp, 2H), 6.54 (s, 1H), 4.99 (m, 1H), 4.96 (m, 1H), 4.73 (m, 1H), 3.95 (s, 3H), 3.84 (s, 3H), 3.33-3.20 (comp, 3H), 1.12 (s, 3H); mass spectrum (CI) m/z+1 373.1277 [$C_{20}H_{21}O_7$ (M+1) requires 373.1287]373(base).

Diastereomeric ratio can be determined by the $^1$HNMR of the aromatic singlet proton: 8A=6.54 ppm, while 8B=6.57 ppm).

(2R*',3R*')-4'-t-butylsilyloxy-1,5-dimethoxy-3'-hydroxy dihydrofuranoxanthone (109). A solution of (108) (0.23 g, 0.62 mmol), TBSCl (0.14 g, 0.93 mmol), imidazole (0.13 g, 1.9 mmol) and DMAP (38 mg, 0.31 mmol) was heated with a heatgun to approx. 85° C. and stirred overnight. TLC (EtOAc) showed that diol still remained, so excess TBSCl (0.14 g), imidazole (0.13 g) and DMAP (40 mg) were added. The reaction was heated with a heatgun in the same manner and stirred 2 h. The reaction was again heated with a heatgun and stirred an additional 2 h. The reaction was concentrated under reduced pressure. The crude product was purified by two successive columns (10% EtOAc/CH$_2$Cl$_2$) to afford 127 mg (42%) of (109B), 54 mg (18%) of a mixed fraction of (109A&B), and 54 mg (18%) of pure (109A). (LH-65-41).

$^1$H NMR 9A (250 MHz, CDCl$_3$) δ 7.84 (d, 1H, J=7.8 Hz), 7.25-7.09 (comp, 2H), 6.3 (s, 1H), 4.99 (app t, 1H, J=9.0 Hz), 3.95 (s, 3H), 3.90 (s, 3H), 3.54 (s, 2H), 3.44-3.27(comp, 2H), 1.13 (s, 3H), 0.90 (s, 3H), 0.09 (s; 6H) $^{13}$C NMR (62.5 MHz) δ 175.1, 165.6, 162.7, 154.1, 147.9, 144.9, 123.9, 123.1, 117.7, 114.6, 106.7, 105.1, 89.8, 88.4, 86.4, 73.5, 67.4, 56.3, 26.9, 25.7, 19.9, –5.6; IR (CH$_2$Cl$_2$) cm$^{-1}$; mass spectrum (CI) m/z+1 487.2141 [$C_{26}H_{35}O_7Si$ (M+1) requires 487.2152] 487(base).

(2R*',3R*')-Psorospermin methyl ether (110). Tetrabutylammonium fluoride (TBAF) (0.06 mL, 0.062 mmol) and (109A) (0.02 g, 0.041 mmol) in THF (1.5 mL) were stirred for 10 min and then concentrated under reduced pressure. The crude product was dissolved in pyridine (0.5 mL), cooled to 0° C. and mesyl chloride (100 μl) was added dropwise. The reaction was stirred for 30 min and monitored by TLC (EtOAc). More MsCl was added (20 μl ) and the reaction stirred 15 min. H$_2$O was added (2 mL) and the mixture was extracted with CHCl$_3$. The cloudy organic layer was washed with 6 M HCl (5 mL), dried (Na$_2$SO$_4$) and concentrated under reduced pressure. To the crude mesylate was added acetone (2 mL), 18-crown-6 (82 mg, 0.031 mmol) and K$_2$CO$_3$ (43 mg, 0.31 mmol). The white suspension was stirred vigorously until TLC (EtOAc) showed that no mesylate remains (1-3 h). The reaction was decanted into a separatory funnel containing EtOAc (20 mL). The flask and remaining K$_2$CO$_3$ were washed with EtOAc (10 mL) which was added to the separatory funnel. The organic layer was washed with sat. NaCl (10 mL), dried (Na$_2$SO$_4$), and concentrated under reduced pressure. The crude product was purified by column chromatography (EtOAc), loading the product onto the column in CH$_2$Cl$_2$, to afford 7 mg (50%) of (±) psorosperrnin methyl ether. The $^1$H NMR and the high resolution mass spectral data corresponds to that expected, as well as to that previously reported (Streelman, dissertation, University of Virginia, 1977). (LH-65-9,10) $^1$H NMR (250 MHz, CDCl$_3$) 7.84 (d, J=6.3 Hz), 7.26-7.11 (complex, 2H), 6.34 (s, 1H), 4.85 (dd, 1H, J=9.9, 7.3 Hz), 4.12 (s, 3H), 4.09 (s, 3H), 3.54 (dd, 1H, J=15.4, 9.9 Hz), 3.34 (dd, 1H, J=15.4, 9.9 Hz), 2.95 (d, 1H, J=4.6 Hz), 2.71 (d, 1H, J=4.6 Hz), 1.43 (s, 3H); $^{13}$C NMR (62.5 MHz) δ 175.1, 165.4, 163.0 154.2, 147.9, 144.9, 123.9, 123.2, 117.8, 114.6, 105.5, 103.9, 89.8, 86.9, 57.7, 56.5, 56.3, 50.9, 28.8, 16.5; mass spectrum (CI) m/z+1 355.1188 [$C_{20}H_{19}O_6$ (M+1) requires 355.1182] 355, 341 (base).

The (2R*,3R*) diasteromer of psorospermin methyl ether (110) (8 mg) was dissolved in the minimum amount of dichloroethane and 100 microlitre injections of the resulting solution were applied to a Phenomenex 25 cm by 10mm HPLC column with a stationary phase of 3,5dinitro urea linked tert-leucine bound to silica gel. The column was eluted at 30° C. with 60% hexane, 20% 1,2-dichloroethane and 20% isopropanol and on repeated injections yield (+) (2S,3S)-psorospermin methyl ether (114)(3 mg) 1H NMR (500 MHz, CDCl3) δ 7.86 (d, 1H) 7.24(t, 1H), 7.15 (d, 1H), 6.37 (s, 1H) 5.29 (s, 1H), 4.91 (dd, 1H), 3.99(s, 3H), 3.47 (dd 1H), 3.32 (dd, 1H), 2.87 (d, 1H), 2.75 (d, 1H) 1.45 (s, 3H) and (–) (2R, 3R)-psorospennin methyl ether (115)(2 mg) 1H NMR (500 MHz, CDCl3) δ 7.86 (d, 1H) 7.24(t, 1H), 7.15 (d, 1H), 6.37 (s, 1H) 5.29 (s, 1H), 4.91 (dd, 1H), 3.99(s, 3H), 3.97 (s, 3H), 3.47 (dd (d, 1H), 2.75 (d, 1H) 1.45 (s, 3H).

Similarly the (2R*,3S*) diastereomer of psorospermin methyl ether (90 mg) was separated to yield (2S,3R)-psorospermin methyl ether (116) (31 mg) 1H NMR (500 MHz, CDCl3) δ 7.83 (d, 1H), 7.24-7.06 (m, 2H), 6.30(s, 1H), 4.85 (dd, 1H), 4.12 (s, 3H), 4.09 (s, 3H), 3.54 (dd, 1H), 3.34 (dd, 1H), 3.50 (dd, 1H), 2.95 (dd, 1H),2.71(d, 1H), 1.43 (d, 1H) and (2R,3S)-psorospermin methyl ether (117) (21 mg) 1H NMR (500 MHz, CDCl3) δ 7.83 (d, 1H), 7.24-7.06 (m, 2H), 6.30(s, 1H), 4.85 (dd, 1H), 4.12 (s, 3H), 4.09 (s, 3H), 3.54 (dd, 1H), 3.50 (dd, 1H), 2.95 (dd, 1H),2.71(d, 1H), 1.43 (d, 1H).

B. Synthesis of Other Psorospermin Analogs

Additional psorospermin analogs were synthesized according to the reaction shown in scheme 14.

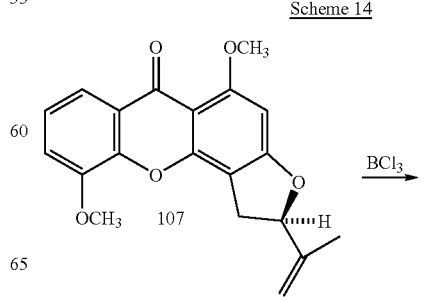

Scheme 14

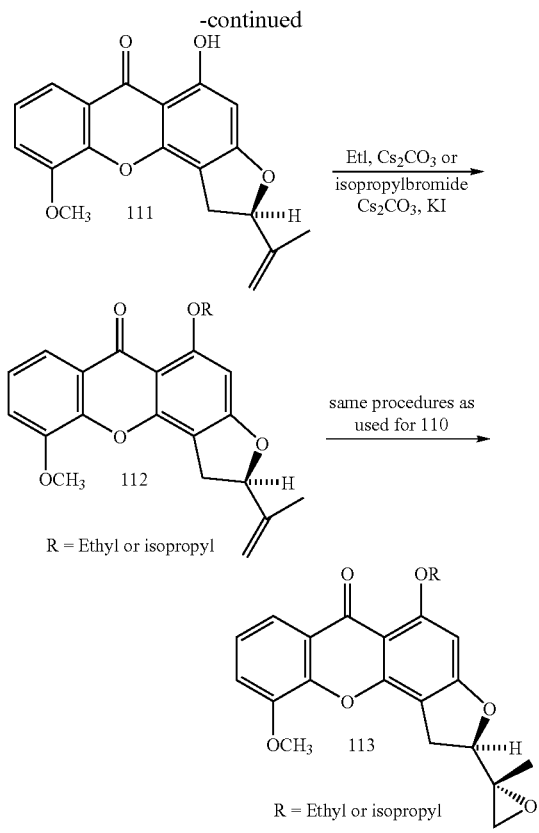

R = Ethyl or isopropyl (±)-1-Hydroxy-2'-isopropenyl-5-methoxy dihydrofuranoxanthone (111). BCl₃ (1.0 M in CH₂Cl₂, 0.30 ml, 0.30 mmol) was added dropwise over five second intervals to methyl ether (107) (0.10 g, 0.30 mmol) in CHCl₃ at 0° C. The reaction was stirred 15 min, and then warmed to rt. TLC (40% EtOAc/hexane) showed that (107) still remains. More BCl₃ (0.10 ml) was added dropwise at rt. After 15 min, TLC showed that (107) still remained so BCl₃ (0.15 ml, followed by 50 µl) was added dropwise at rt. The reaction was poured into a separatory funnel containing H₂O (20 mL), and extracted with CH₂Cl₂ (2×10 mL). The organic layers were combined, washed with sat. NaCl and dried (Na₂SO₄). The crude product was purified by column chromatography eluting with 40% EtOAc/hexane to afford 84 mg (88%) of (111) as a yellow solid. (LH-66-38)

¹H NMR (250 MHz, CDCl₃) 13.1 (s, 1H), 7.76 (d, 1H, J=6.0 Hz), 7.26-7.16 (comp, 2H), 6.30 (s, 1H), 5.37 (app. t, 1H, J=8.5 Hz), 5.11 (s, 1H), 4.95 (s, 1H), 3.98 (s, 3H), 3.50 (dd 1H, J=15.3, 9.96 Hz), 3.18 (dd, 1H, J=15.3, 7.6 Hz), 2.04 (s, 3H).

General Procedure For: (±)-1-Alkylether-2'-isopropenyl-5-methoxy dihydrofuranoxanthone (112). Cs₂CO₃ (80.0 mg, 0.25 mmol) was added to phenol (111) (40 mg, 0.12 mmol) and EtI (15 µL, 0.19 mmol) in DMF (3 mL) at rt. After 3 h at 50° C., more EtI (10 µL) was added and the reaction stirred an addition 1 h. 2M HCl was added slowly until the reaction mixture was acidic by pH paper. After warming to rt, the reaction was diluted with CH₂Cl₂ (10 mL) and H₂O (10 mL). The organic layer was washed with brine (400 mL), dried (Na₂SO₄) and concentrated under reduced pressure to provide a yellow solid. Column chromatography eluting with 40% EtOAc/hex affords (34 mg, 79%) of 12 a white solid. (LH-66-41)

Isopropyl analog (112): ¹H NMR (250 MHz, CDCl₃) 7.86 (d, 1H, J=6.3 Hz), 7.28-7.10 (comp., 2H), 6.37 (s, 1H), 5.37 (app. t, 1H, J=8.5 Hz), 5.12 (s, 1H), 4.96 (s, 1H), 4.62 (sex, 1 H, J=6.0 Hz), 3.97 (s, 3H), 3.56 (dd, 1H, J=15.3, 9.7 Hz), 3.22 (dd, 1H, J=7.8, 15.3 Hz), 1.81 (s, 3H), 1.49 (d, 2H, J=6.0 Hz); ¹³C NMR (62.5 MHz) δ 175.1, 165.5, 161.5, 154.4, 147.9, 144.9, 143.2, 124.1, 123.0,117.8, 114.6, 112.6, 107.7, 104.5, 92.5, 88.1, 72.1, 56.3, 31.4, 21.9, 17.0; mass spectrum (CI) m/z+1 357.1549 [C₂₂H₂₃O₅ (M+1) requires 367.1545] 367, 154 (base).

Ethyl analog (112): ¹H NMR (250 MHz, CDCl₃) 7.86 (d, 1H, J=6.3 Hz), 7.25-7.08 (comp., 2H), 6.33 (s, 1H), 5.36 (app. t, 1H, J=8.7 Hz), 5.10 (s, 1H), 4.95 (s, 1H), 4.15 (q, 2 H, J=7.0 Hz), 3.96 (s, 3H), 3.56 (dd, 1H, J=15.3, 9.7 Hz), 3.20 (dd, 1H, J=7.8, 15.3 Hz), 1.79 (s, 3H), 1.55 (t, 4H, J=7.0 Hz); mass spectrum (CI) m/z+1 353.1392 [C₂H₂₁O₅ (M+1) requires 353.1389] 353, 307, 154 (base).

(2R*',3R*')-1-Ethoxy-psorospermin methyl ether (113). Procedure is same as that used to make compounds (108), (109) and (110). ¹H NMR (250 MHz, CDCl₃) 7.86 (d, 1H, J=6.3 Hz), 7.25-7.13 (comp., 2H), 6.35 (s, 1H), 4.83 (d, 1H, J=9.9, 7.3 Hz), 4.15 (q, 2H, J=7.0 Hz), 3.99 (s, 3H), 3.49 (dd, 1H, J=15.4, 9.9 Hz), 3.20 (dd, 1H, J=15.4, 8.0 Hz), 2.95 (d, 1H, J=4.6 Hz), 2.72 (d, 1H, J=4.6 Hz), 1.55 (t, 4H, J=7.0 Hz). (LH-66-43)

(2R*',3R*')-1-Isopropoxy-psorospermin methyl ether (113). Procedure is same as that used to make compounds (108), (109) and (110). ¹H NMR (250 MHz, CDCl₃) 7.86 (d, 1H, J=6.3 Hz), 7.26-7.12 (comp., 2H), 6.36 (s, 1H), 4.83 (d, 1H, J=9.3, 7.4 Hz), 4.62 (sex, 1H, J=6.2 Hz), 3.98 (s, 3H), 3.52 (dd, 1H, J=15.1, 7.1 Hz), 3.20 (dd, 1H, J=9.9, 15.1 Hz), 2.95 (d, 1H, J=4.6 Hz), 2.72 (d, 1H, J=4.6 Hz), 1.57-1.53 (comp, 6H); mass spectrum (CI) m/z+1 383.1500 [C₂₂H₂₃O₆ (M+1) requires 383.1495] 383 (base), 341, 154. (LH-66-48b)

REFERENCES

The following references, to the extent that they provide exemplary procedural or other details supplementary to those set forth herein, are specifically incorporated herein by reference:

Ahluwalia, V. K.; Tehim, A. K. (1984) A new route towards the synthesis of dihydropyranoxanthones. *Heterocycles* 22, 2703-2711.

Ausubel, F. M., ed. (1988) *Current Protocols in Molecular Biology*, John Wiley and Sons, NY.

Baguley, B. (1991) DNA intercalating anti-tumour agents. *Anti-Cancer Drug Des.* 6, 1-35.

Bea, S.; Tort, F.; Pinyol, M.; Puig, X.; Hernandez, L.; Hernandez, S.; Fernandez, P.; van Lohuizen, M.; Colomer, D.; Campo, E. (2001) BMI-1 Gene Amplification and Overexpression in Hematological Malignancies Occur Mainly in Mantle Cell Lymphomas. *Cancer Res.* 61, 2409-2412.

Brill, S. J.; DiNardo, S.; Voelkel-Meiman, K.; Sternglanz, R. (1987a) Need for DNA topoisomerase activity as a swivel for DNA replication for transcription of ribosomal RNA. *Nature* 326,414-416.

Brill, S. J.; DiNardo, S.; Voelkel-Meiman, K.; Sternglanz, R. (1987b) DNA topoisomerase activity is required as a swivel for DNA replication and for ribosomal RNA transcription. *NCI Monogr.* 11-15.

Capranico, G.; Butelli, E.; Zunino, F. (1995) Change of the sequence specificity of daunorubicin-stimulated topoisomerase II DNA cleavage by epimerization of the amino group of the sugar moiety. *Cancer Res.* 55, 312-317.

Capranico, G.; Binaschi, M. (1998) DNA sequence selectivity of topoisomerases and topoisomerase poisons. *Biochim. Biophys. Acta* 1400, 185-194.

Cassady, J. M.; Byrn, S. R.; McKenzie, A. T.; Ho, D. K. (1987a) $O^5$-Methyl-(±)-(2'R,3'S)-psorospermin. *J. Org. Chem.* 52, 342-347.

Cassady, J. M.; Reddy, K. S.; Ko, O. H.; Ho, D. (1987b) A novel enantioselective cyclization of a chiral epoxide to a benzofuran system. *Tetrahedron Lett.* 28, 3075-3078, and references therein.

Cassady, J. M.; Baird, W. M.; Chang C. J. (1990) *J. Nat. Prod.* 53, 23-41.

Cockerill, G. S.; Levett, P. C.; Whiting, D. A. (1995) Synthesis of novel inhibitors of electron transport. *J. Chem. Soc. Perkin Trans.* 1, 1103-1113.

Covey, J. M.; Kohn, K. W.; Kerrigan, D.; Tilchen, E. J.; Pommier, Y. (1988) Topoisomerase II-mediated DNA damage produced by 4'-(9-acridinylamino)methane-sulfon-m-anisidide and related acridines in L1210 cells and isolated nuclei: relation to cytotoxicity. *Cancer Res.* 48, 860-865.

Cullen, B. R. (1987) Use of eukaryotic expression technology in the functional analysis of cloned genes. *Methods Enzymol.* 152, 684-704.

Cummings, J.; Hadfield, J. A.; Meikle, I.; McGown, A. T.; Smyth, J. F. (1996) *Anticancer Drug* 7, 636-641.

de Wet, J. R.; Wood, K. V.; DeLuca, M.; Helinski, D. R.; Subramani, S. (1987) Firefly luciferase gene: structure and expression in mammalian cells. *Mol. Cell Biol.* 7, 725-737.

Dean, F. M. (1973) The total synthesis of naturally occurring oxygen ring compounds. In *The Total Synthesis of Natural Products*, Vol. 1; ed. Apsimon, J. (John Wiley & Sons, New York), pp. 467-562.

Dingemans, A. -M. C; Pinedo, H. M.; Giaccone, G. (1998) Clinical resistance to topoisomerase-targeted drugs. *Biochim. Biophys. Acta* 1400, 275-288.

Eckardt, J. R.; Burris, H. A.; Rothenberg, M. L.; Von Hoff, D. D.; Kuhn, J. G. (1993) Topoisomerase II inhibitors: promising novel compounds. *Contemporary Oncology* 3, 47-60.

Gopalakrishnan, S.; Liu, X.; Patel, D. (1992) Solution structure of the covalent sterigmatocystin-DNA adduct. *Biochemistry* 31, 10790-10801.

Hammond, L. A.; Eckardt, J. R.; Ganapathi, R.; Burris, H. A.; Rodriguez, G. A.; Eckhardt. S. G.; Rothenberg, M. L.; Weiss, G. R.; Kuhn, J. G.; Hodges, S.; Von Hoff, D. D.; Rowinsky, E. K. (1998) A phase I and translational study of sequential administration of the topoisomerase I and II inhibitors topotecan and etoposide. *Clin. Cancer Res.* 4, 1459-1467.

Hansen, M.; Lee, S. J.; Cassady, J. M.; Hurley, L. (1996) Molecular Details of the Structure of a Psorospermin-DNA Covalent/Intercalation Complex and Associated DNA Sequence Selectivity. *J. Am. Chem. Soc.* 118, 5553-5561.

Hansen, M.; Hurley, L. H. (1995) Altromycin B Threads the DNA Helix Interacting with both the Major and the Minor Grooves to Position Itself for Site-Directed Alkylation of Guanine N7. *J. Am. Chem. Soc.* 117, 2421-2429.

Hansen, M.; Yun, S.; Hurley, L. H. (1995) Hedamycin Intercalates the DNA Helix and, Through Carbohydrate-Mediated Recognition in the Minor Groove, Directs N7-Alkylation of Guanine in the Major Groove in a Sequence-Specific Manner. *Chem. Biol.* 2, 229-240.

Hayashi, T.; Uozumi, Y.; Kato, K.; Uozumi, Y.; Kyoto, H.; Ogasawara, M. (1999) Design and preparation of 3,3'-disubstituted 2,2'-bis(oxazoyl)-1,1'-binaphthyls(boxax): New chiral bis(oxazline) ligands for catalytic asymmetric Wacker-type cyclization. *J. Org. Chem.* 64, 1620-1625, and references therein.

Hermine, O.; Haioun, C.; Lepage, E.; d'Agay M. F.; Briere, J.; Lavignac, C.; Fillet, G.; Salles, G.; Marolleau, J. P.; Diebold, J.; Reyas, F.; Gaulard, P. (1996) Prognostic significance of Bcl-2 protein expression in aggressive non-Hodgkin's lymphoma: groupe d'etude des lymphomas de l'adulte (GELA). *Blood* 87, 265-272.

Hill, M. E.; MacLennan, K. A.; Cunningham, D. C.; Vaughan Hudson, B.; Burke, M.; Clarke, P.; Di Stefano, F.; Anderson, L.; Vaughan Hudson, G.; Mason, D.; Selby, P.; Linch, D. C. (1996) Prognostic significance of Bcl-2 expression and Bcl-2 major breakpoint region rearrangement in diffuse large cell non-Hodgkin's lymphoma: a British national lymphoma investigation study. *Blood* 88, 1046-1051.

Hlubucek, J.; Ritchie, E.; Taylor, W. C. (1969) Synthesis of 2,2-Dimethylchromenes. *Tetrahedron Lett.* 1369-1370.

Hurley, L. H.; Fellows, I. M. (2000) Progress towards the total synthesis of psorospermin, $220^{th}$ National American Chemical Society Meeting, Washington, D.C.

Ireland, R. E.; Smith, M. G. (1988) 3-Acyltetramic acid antibiotics. 2. Synthesis of (+)-streptolic acid. *J. Am. Chem. Soc.* 110, 854860.

Kelly, J. W.; Robinson, P. L.; Evans, S. A. Jr. (1985) Diethoxydiphenylpolystryrylphosphorane: a new polymeric reagent for the efficient cyclodehydration of simple diols. *J. Org. Chem.* 50,5007-5009.

Kitamura, M.; Isobe, M.; Ichikawa, Y.; Goto, T. (1984) Stereocontrolled total synthesis of (-)-maytansinol. *J. Am. Chem. Soc.* 106, 3252-3257.

Kolb, H. C.; Vannieuwenhze, M. S.; Sharpless, K. B. (1994) Catalytic asymmetric dihydroxylation. *Chem. Rev.* 94, 2483-2547.

Kupchan, S. M.; Streelman, D. R. (1977) Ph.D. Thesis, University of Virginia, Charlottesville, Va.

Kupchan, S. M.; Streelman, D. R.; Sneeden, A. T. (1980) *J. Nat. Prod.* 43, 296-301.

Kwok, Y.; Zweng, Q.; Hurley, L. (1998) *Proc. Natl. Acad. Sci. USA* 95, 13531-13536.

Kwok, Y.; Hurley, L. (1998) Topoisomerase II Site-Directed Alkylation of DNA by Psorospermin and Its Effect on Topoisomerase 11-Mediated DNA Cleavage. *J. Biol. Chem.* 273, 33020-33026.

Lee, M. P.; Sander, M.; Hsieh, T. S. (1989) *J. Biol. Chem.* 264, 21779-21787.

Levine, E. G.; Arthur, D. C.; Frizzera, G.; Peterson, B. A.; Hurd, D. D.; Bloomfield, C. D. (1985) There are differences in cytogenetic abnormalities among histologic subtypes of the non-Hodgkin's lymphomas. *Blood* 66, 1414-1422.

Liu, L. F.; Wang, J. C. (1987) Supercoiling of the DNA template during transcription. *Proc. Natl. Acad. Sci. U.S.A.* 84, 7024-7027.

Liu, L. F. (1989) *Annu. Rev. Biochem.* 58, 351-375.

Locksley, H. D.; Quillinan, A. J.; Scheinmann, F. (1971) Extractives from *Guttiferae*. Part XXIII. An unambiguous synthesis of 6-deoxyjacareubin and related 3,3- and 1,1-dimethylallyl and annulated xanthones. *J. Chem. Soc. (C)*, 3804-3814.

Miyashita, T.; Reed, J. C. (1992) Bcl-2 gene transfer increases relative resistance of S49.1 and WEHI7.2 lymphoid cells to cell death and DNA fragmentation induced by glucocorticoids and multiple chemotherapeutic drugs. *Cancer Res.* 52, 5407-5411.

Nabiev, I.; Chourpa, I.; Riou, J.; Nguyen, C.; Lavelle, F.; Manfait, M. (1994) *Biochemistry* 33, 9013-9023.

NCI Developmental Therapeutics Web Site, http://www.dtp.nci.nih.gov/docs/cancer/searches/cancer_open_compounds.html.

Osheroff, N.; Zechiedrich, E. L.; and Gale, K. C. (1991) *Bioessays* 13, 269-275.

Osheroff, N., Corbett, A. H., and Robinson, M. J. (1994) *Adv. Pharmacol.* 29B, 105-126.

Park, K. H.; Yoon, Y. J.; Lee, S. G. (1994) Efficient cleavage of terminal acetonide group: chirospecific synthesis of 2,4-dideoxy-2,5-imino-d-mannitol. *Tetrahedron Lett.* 35, 9737-9740.

Pommier, Y. (1997) in Cancer Therapeutics: Experimental and Clinical Agents (Teicher, B. A., ed), pp. 153-174, Humana Press, Totowa, N.J.

Permana, P. A.; Ho, D. K.; Cassady, J. M.; Snapka, R. M. (1994) Mechanism of action of the antileukemic xanthone psorospermin: DNA strand breaks, abasic sites, and protein-DNA cross-links. *Cancer Res.* 54, 3191-3195.

Pommier, Y.; Koh, K. W. (1989) in *Developments in Cancer Chemotherapy*, R. I. Glazer, Ed., CRC Press, Boca Raton, Fla., pp. 175-195.

Pommier, Y.; Orr, A.; Kohn, K. W.; Riou, J. F. (1992) *Cancer Res.* 52, 3125-3130.

Remington's Pharmaceutical Sciences, 18th Ed. Mack Printing Company, 1990.

Robinson, M. J., and Osheroff, N. (1991) *Biochemistry* 30, 1807-1813.

Rosenthal, N. (1987) Identification of regulatory elements of cloned genes with functional assays. *Methods Enzymol.* 152, 704-720.

Schenborn, E.; Goiffon, V. (1991) *Promega Notes* 33, 8.

Schultz, M. C.; Brill, S. J.; Ju, Q.; Sternglanz, R.; Reeder, R. H. (1992) Topoisomerases and yeast rRNA transcription: negative supercoiling stimulates initiation and topoisomerase activity is required for elongation. *Genes Dev.* 6, 1332-1341.

Sharpless, K. B.; Amberg, W.; Bennani, Y. L.; Crispino, G. A.; Hartung, J.; Jeong, K. S.; Kwong, H. L.; Morikawa, K.; Wang, Z. M.; Xu, D.; Zhang, X. L. (1992) The osmium-catalyzed asymmetric dihydroxylation—a new ligand class and a process improvement. *J. Org. Chem.* 57, 2768-2771.

Sun, D.; Hansen, M.; Hurley, L. H. Molecular Basis for the DNA Sequence Specificity of the Pluramycins. A Novel Mechanism Involving Groove Interactions Transmitted through the Helix via Intercalation to Achieve Sequence Selectivity at the Covalent Bonding Step. *J. Am. Chem. Soc.* 117, 2430-2440 (1995).

Taylor, W. C.; Hlubucek, J.; Ritchie, E. (1969) Synthesis of o-Isopentenylphenols. *Chem. Ind.*, 1780-1781.

Taylor, W. C.; Hlubucek, J.; Ritchie, E. (1971) Synthesis of o-Isopentenylphenols. *Aust. J Chem.* 24, 2355-2363.

Wang, J. (1996) *Annu. Rev. Biochem.* 65, 635-692.

Waters, J. S.; Webb, A.; Cunningham, D.; Clarke, P. A.; Raynaud, F.; di Stefano, F.; Cotter, F. E. (2000) Phase I clinical and pharmacokinetic study of bcl-2 antisense oligonucleotide therapy in patients with non-Hodgkin's lymphoma. *J. Clin. Oncol.* 18, 1812-1823.

Watt, P. M., and Hickson, I. D. (1994) *Biochem. J.* 303, 681-695.

Webb, A.; Cunningham, D.; Cotter, F.; Clarke, P. A.; di Stefano, F.; Ross, P.; Corbo, M.; Dziewanowska, Z. (1997) BCL-2 antisense therapy in patients with non-Hodgin lymphoma. *Lancet* 349,1137-1141.

Wood, K. V. (1990) *Promega Notes* 28, 1.

Yunis, J. J.; Oken, M. M.; Kaplan, M. E.; Ensrud, K. M.; Howe, R. R.; Theologides, A. (1982) Distinctive chromosomal abnormalities in histologic subtypes of non-Hodgkin's lymphoma. *N. Engl. J. Med.* 307, 1231-1236.

Zwelling, L. A.; Michaels, S.; Erickson, L. C.; Ungerleider, R. S.; Nichols, M.; Kohn, K. W. (1981) Protein-associated deoxyribonucleic acid strand breaks in L1210 cells treated with the deoxyribonucleic acid intercalating agents 4'-(9-acridinylamino) methanesulfon-m-anisidide and adriamycin. *Biochemistry* 20, 6553-6563.

What is claimed is:

1. A method of inhibiting cell proliferation, the method comprising contacting a cancer cell with an effective amount of a compound having the formula:

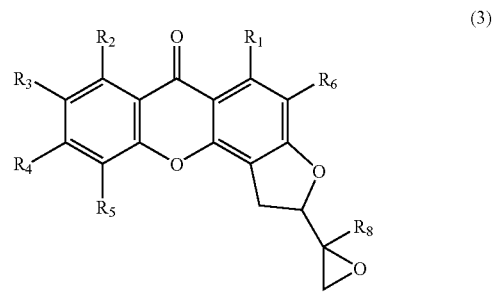

(3)

wherein each $R_1$-$R_4$ and $R_6$ is independently H, OH, O-alkyl, halogen, or alkyl;

$R_5$ is H, O-alkyl, or alkyl; and $R_8$ is alkyl.

2. A method to inhibit proliferation of a cancer cell, wherein the cancer cell is a pancreatic cancer cell, prostate cancer cell, myeloma cell, ovarian cancer cell, or breast cancer cell, which comprises contacting said cell with an effective amount of a compound of the formula:

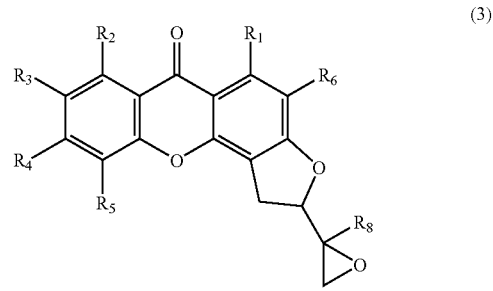

(3)

wherein $R_1$-$R_4$, $R_6$ and $R_8$ are as defined in claim 1 and $R_5$ is H, OH, O-alkyl or alkyl.

3. The method of claim 2, wherein the cancer cell is a multi-drug resistant (MDR) cancer cell.

4. The method of claim 3, wherein the MDR cancer cell is resistant to a topoisomerase II inhibitor.

5. The method of claim 3, wherein MDR is mediated by MRP-1 or glycoprotein.

6. The method of claim 2, wherein the cell is in a mammal.

* * * * *

UNITED STATES PATENT AND TRADEMARK OFFICE
CERTIFICATE OF CORRECTION

PATENT NO.        : 7,244,760 B2                                Page 1 of 1
APPLICATION NO.   : 10/152152
DATED             : July 17, 2007
INVENTOR(S)       : Laurence Hurley et al.

It is certified that error appears in the above-identified patent and that said Letters Patent is hereby corrected as shown below:

Title page, item [57], line 1, delete "dihydroflranoxanthone" and insert --dihydrofuranoxanthone-- therefor.

Signed and Sealed this

Thirteenth Day of November, 2007

JON W. DUDAS
*Director of the United States Patent and Trademark Office*